United States Patent [19]

Nakamizo et al.

[11] 4,446,141
[45] May 1, 1984

[54] HYPOTENSIVE PIPERIDINE DERIVATIVES

[76] Inventors: Nobuhiro Nakamizo, 1704-22, Honmachida, Machida-shi, Tokyo, 194; Hiroyuki Obase, 9-9, Naka-machi 3-chome, Machida-shi, Tokyo, 194; Kazuhiro Kubo, 625-11, Kashiwakubo, Shuzenji-machi, Tagata-gun, Shizuoka, 410-24; Yutaka Kasuya, 1-61, Komukainishi-machi, Saiwai-ku, Kawasaki-shi, Kanagawa, 210, all of Japan

[21] Appl. No.: 191,339

[22] PCT Filed: Jun. 1, 1979

[86] PCT No.: PCT/JP79/00141
§ 371 Date: Feb. 2, 1980
§ 102(e) Date: Jan. 31, 1980

[87] PCT Pub. No.: WO80/00024
PCT Pub. Date: Jan. 10, 1980

[30] Foreign Application Priority Data

Jun. 2, 1978 [JP] Japan ................................ 53/66548

[51] Int. Cl.$^3$ .................. A61K 31/445; C07D 401/04
[52] U.S. Cl. ................................. 424/267; 424/263; 546/199; 546/221; 546/271
[58] Field of Search .............. 546/199, 271; 424/263, 424/267

[56] References Cited

U.S. PATENT DOCUMENTS

| | | | |
|---|---|---|---|
| 3,318,900 | 5/1967 | Janssen | 546/199 |
| 3,910,930 | 10/1975 | Janssen | 424/267 X |
| 3,929,801 | 12/1975 | Janssen | 424/267 X |
| 4,031,226 | 6/1977 | Soudijn et al. | 546/199 X |
| 4,264,613 | 4/1981 | Regnier et al. | 546/199 X |
| 4,344,948 | 8/1982 | Takai et al. | 546/199 X |

FOREIGN PATENT DOCUMENTS

| | | |
|---|---|---|
| 0008259 | 2/1980 | European Pat. Off. |
| 42-2062 | 1/1967 | Japan . |
| 47-7267 | 3/1972 | Japan . |
| 49-41381 | 4/1974 | Japan . |
| 50-84579 | 7/1975 | Japan .................................. 546/199 |
| 52-27775 | 3/1977 | Japan . |
| 989755 | 4/1965 | United Kingdom ................ 546/199 |
| 10463112 | 10/1966 | United Kingdom . |
| 1404003 | 8/1975 | United Kingdom ................ 546/201 |

OTHER PUBLICATIONS

Wellens, D., et al., *Arch. Int. Pharmacodyn.* 215, 91-103, (1975).

Primary Examiner—Richard A. Schwartz
Attorney, Agent, or Firm—Fitzpatrick, Cella, Harper & Scinto

[57] ABSTRACT

The present invention relates to a novel compound represented by the general formula:

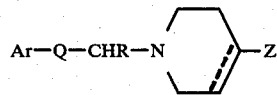

wherein Ar represents a naphthyl, phenyl or substituted phenyl group, Q represents

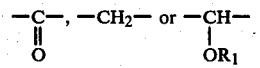

wherein $R_1$ represents a hydrogen atom, or an alkyl, alkanoyl or alkoxycarbonyl group, R represents a hydrogen atom or an alkyl group, and Z represents a substituted benzimidazolinyl group; the broken line in piperidine ring means that 3,4-positions in the piperidine ring are saturated or form a double bond. Said compound and the pharmaceutically acceptable acid addition salts thereof have a hypotensive action and therefore are useful as medicine.

13 Claims, No Drawings

HYPOTENSIVE PIPERIDINE DERIVATIVES

Technical Field

The present invention relates to novel piperidine derivatives, acid addition salts thereof and pharmaceutical compositions containing the same.

The piperidine derivatives are compounds represented by the general formula (I):

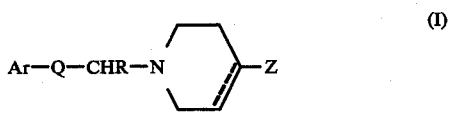

[wherein Ar represents a naphthyl, phenyl or substituted phenyl group, Q represents

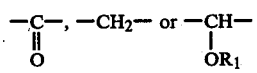

(wherein $R_1$ is a hydrogen atom or an alkyl, alkanoyl or alkyoxycarbonyl group), R represents a hydrogen atom or an alkyl group, and Z represents a substituted benzimidazolinyl group; the broken line in piperidine ring means that the 3,4-positions in the piperidine ring are saturated or form a double bond]. The compounds represented by the general formula (I) and the pharmaceutically acceptable acid addition salts thereof have a hypotensive action, and therefore are useful as medicine.

Background Art

As the compounds structurally analogous to the compounds of the general formula (I), there have been known some compounds wherein arylalkyl hyrocarbon having an aromatic substituent and containing 3 or 4 carbon atoms in the aliphatic moiety is bonded to the nitrogen atom in the piperidine ring of the general formula (I). For example, the following compounds are commercially available as tranquilizers.

4'-fluoro-4-[4-(2-oxobenzimidazolin-1-yl) piperid-1-yl] butyrophenone (trade name: Benperidol)

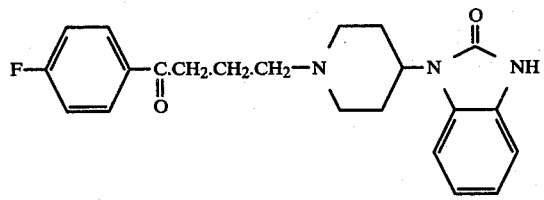

1-{1-[4-(P-fluorophenyl)-4-oxobutyl]-1,2,3,6-tetrahydro-4-pyridyl}-2-benzimidazolinone (trade name: Droperidol)

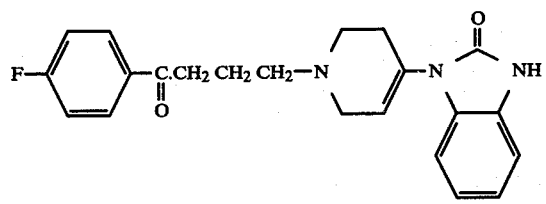

1-{1-[4,4-bis(P-fluorophenyl)butyl]-4-piperidyl}-2-benzimidazolinone (trade name: Pimozide)

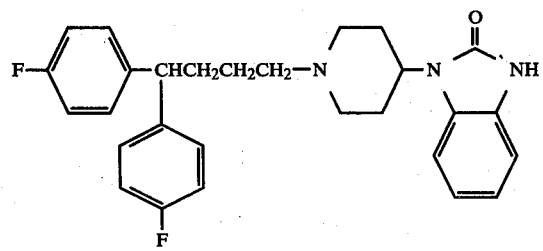

Compounds having excellent pharmacological activities are always in demand. In order to obtain such compounds, studies have been made on piperidine derivatives and as a result, it has been found that novel piperidine derivatives represented by the general formula (I) have a hypotensive action.

Disclosure of Invention

The present invention relates to the compounds represented by the above general formula (I), acid addition salts thereof and their use as medicine.

Each symbol in the general formula (I) is explained in detail below.

The substituent in the substituted phenyl group represented by Ar is a straight- or branched-chain alkoxy group having 1–6 carbon atoms, a hydroxy group, a benzyloxy group or an alkylenedioxy group having 1–3 carbon atoms, and the substituted phenyl group has 1–5 substituents at the benzene ring.

Examples of the substituent are alkoxy groups such as methoxy, ethoxy, n-propoxy, i-propoxy and t-butoxy, a benzyloxy group and alkylenedioxy groups such as methylenedioxy, ethylenedioxy and propylenedioxy.

Examples of the substituted phenyl group are 3,4-dihydroxyphenyl, 3-hydroxyphenyl, 3,4-dimethoxyphenyl, 3,4-methylenedioxyphenyl, 3,4,5-trimethoxyphenyl, 3,4-dibenzyloxyphenyl and 3-benzyloxyphenyl.

Examples of the naphthyl represented by Ar are 1-naphthyl and 2-naphthyl.

The alkyl group represented by $R_1$ in the definition of Q is straight- or branched-chain alkyl having 1–5 carbon atoms such as methyl, ethyl, n-propyl, i-propyl and n-butyl. The alkanoyl group represented by $R_1$ has the alkyl moiety the definition of which is the same as that of the above-mentioned alkyl group, and the examples thereof are acetyl and propionyl.

The alkyl group represented by R has the same definition as the alkyl group represented by $R_1$.

Z is a substituted benzimidazolinyl group represented by the following formula (a) or (b).

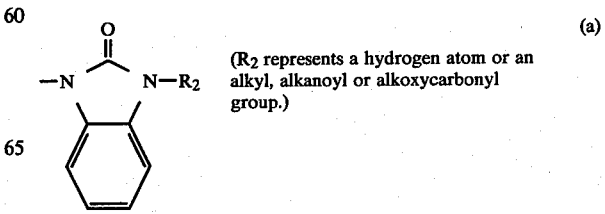

($R_2$ represents a hydrogen atom or an alkyl, alkanoyl or alkoxycarbonyl group.)

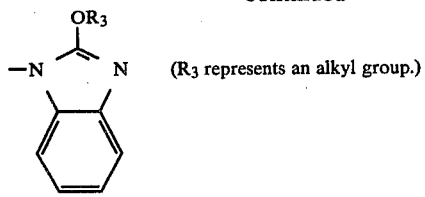

(R₃ represents an alkyl group.)

The alkyl groups represented by $R_2$ and $R_3$ have the same definition as the alkyl group represented by $R_1$. The alkanoyl group represented by $R_2$ has the same definition as the alkanoyl group represented by $R_1$. The alkoxycarbonyl group represented by $R_2$ is alkoxycarbonyl having 2–6 carbon atoms such as methoxycarbonyl, ethoxycarbonyl, propoxycarbonyl and t-butoxycarbonyl.

Acid addition salts of the compounds represented by the general formula (I) are, for example, inorganic acid addition salts such as hydrochloride, hydrobromide, hydriodide, sulfate and phosphate and organic acid addition salts such as acetate, benzoate, maleate, fumarate, succinate, tartrate, citrate, oxalate, glyoxylate, aspartate and methanesulfonate.

Examples of the present compounds are tabulated in the following Table 1. Table 2 shows structures and Tables 3-1, 2 and 3 show properties of the compounds. The numbers assigned to the compounds correspond to the numbers of Examples.

TABLE I

| Compound No. (Example No.) | Compound |
|---|---|
| 1 | 1-[2-oxo-2-(3,4-dimethoxyphenyl)-1-ethyl]-4-(2-keto-1-benzimidazolinyl)-piperidine |
| 2 | 1-[2-oxo-2-(3,4-methylenedioxyphenyl)-1-ethyl]-4-(2-keto-1-benzimidazolinyl)-piperidine |
| 3 | 1-[2-oxo-2-(2-naphthyl)-1-ethyl]-4-(2-keto-1-benzimidazolinyl)-piperidine |
| 4 | 1-[2-oxo-2-(3,4-dimethoxyphenyl)-1-ethyl]-4-(2-keto-3-acetyl-1-benzimidazolinyl)-piperidine |
| 5 | 1-[2-oxo-2-(3,4-methylenedioxyphenyl)-1-ethyl]-4-(2-ethoxy-1-benzimidazolinyl)-piperidine |
| 6 | 1-[2-oxo-2-(3,4-dihydroxyphenyl)-1-ethyl]-4-(2-keto-1-benzimidazolinyl)-piperidine |
| 7 | 1-[2-hydroxy-2-(3,4-methylenedioxyphenyl)-1-ethyl]-4-(2-keto-1-benzimidazolinyl)-piperidine |
| 8 | 1-[2-hydroxy-2-(3,4-dimethoxyphenyl)-1-ethyl]-4-(2-keto-1-benzimidazolinyl)-piperidine |
| 9 | 1-[2-hydroxy-2-(3,4-dihydroxyphenyl)-1-ethyl]-4-(2-keto-1-benzimidazolinyl)-piperidine |
| 10 | 1-[2-hydroxy-2-(2-naphthyl)-1-ethyl]-4-(2-keto-1-benzimidazolinyl)-piperidine |
| 11 | 1-[2-hydroxy-2-(3,4-methylenedioxyphenyl)-1-ethyl]-4-(2-ethoxy-1-benzimidazolinyl)-piperidine |
| 12 | 1-[2-(3,4-methylenedioxyphenyl)-1-ethyl]-* 4-[-keto-1-benzimidazolinyl]-1,2,5,6-tetrahydropyridine |
| 13 | 1-[2-(3,4-methylenedioxyphenyl)-1-ethyl]-4-(2-keto-1-benzimidazolinyl)-piperidine |
| 14 | 1-[2-(3,4-dimethoxyphenyl)-1-ethyl]-4-(2-keto-1-benzimidazolinyl)-piperidine |
| 15 | 1-[2-(3,4-dihydroxyphenyl)-1-ethyl]-4-(2-keto-1-benzimidazolinyl)-piperidine |
| 16 | 1-[3-oxo-3-(3,4-dimethoxyphenyl)-2-propyl]-4-(2-keto-1-benzimidazolinyl)-piperidine |
| 17 | 1-[3-oxo-3-(3,4-methylenedioxyphenyl)-2-propyl]-4-(2-keto-1-benzimidazolinyl)-piperidine |
| 18 | 1-[3-oxo-3-(3,4-dihydroxyphenyl)-2-propyl]-4-(2-keto-1-benzimidazolinyl)-piperidine |
| 19 | 1-[3-hydroxy-3-(3,4-methylenedioxyphenyl)-2-propyl]-4-(2-keto-1-benzimidazolinyl)-piperidine |
| 20 | 1-[3-hydroxy-3-(3,4-dihydroxyphenyl)-2-propyl]-4-(2-keto-1-benzimidazolinyl)-piperidine |
| 21 | 1-[3-hydroxy-(3-hydroxyphenyl)-2-propyl]-4-(2-keto-1-benzimidazolinyl)-piperidine |
| 22 | 1-[3-hydroxy-3-(3,4-dimethoxyphenyl)-2-propyl]-4-(2-keto-1-benzimidazolinyl)-piperidine |
| 23 | 1-[2-acetoxy-2-(3,4-methylenedioxyphenyl)-1-ethyl]-4-(2-keto-1-benzimidazolinyl)-piperidine |
| 24 | 1-[2-oxo-2-phenyl-1-ethyl]-4-(2-keto-1-benzimidazolinyl)-piperidine |
| 25 | 1-[2-hydroxy-2-phenyl-1-ethyl]-4-(2-keto-1-benzimidazolinyl)-piperidine |
| 26 | 1-[2-oxo-2-(3,4-methylenedioxyphenyl)-1-ethyl]-4-(3-ethyl-2-keto-1-benzimidazolinyl)-piperidine |
| 27 | 1-[2-hydroxy-2-(3,4-methylenedioxyphenyl)-1-ethyl]-4-(3-ethyl-2-keto-1-benzimidazolinyl)-piperidine |
| 28 | 1-[2-oxo-2-(3,4,5-trimethoxyphenyl)-1-ethyl]-4-(2-keto-1-benzimidazolinyl)-piperidine |
| 29 | 1-[2-hydroxy-2-(3,4,5-trimethoxyphenyl)-1-ethyl]-4-(2-keto-1-benzimidazolinyl)-piperidine |
| 30 | 1-[3-oxo-3-(3,4,5-trimethoxyphenyl)-2-propyl]-4-(2-keto-1-benzimidazolinyl)-piperidine |
| 31 | 1-[3-hydroxy-3-(3,4,5-trimethoxyphenyl)-2-propyl]-4-(2-keto-1-benzimidazolinyl)-piperidine |
| 32 | 1-[3-acetoxy-3-(3,4-dimethoxyphenyl)-2-propyl]-4-(3-acetyl-2-keto-1-benzimidazolinyl)-piperidine |
| 33 | 1-[3-hydroxy-3-(3,4-dimethoxyphenyl)-2-propyl]-4-(3-acetyl-2-keto-1-benzimidazolinyl)-piperidine |
| 34 | 1-[3-acetoxy-3-(3,4-dimethoxyphenyl)-2-propyl]-4-(2-keto-1-benzimidazolinyl)-piperidine |
| 35 | 1-[2-oxo-2-(3,4-dimethoxyphenyl)-1-ethyl]-4-(2-keto-3-ethoxycarbonyl-1-benzimidazolinyl)-piperidine |

*3,4-position of piperidine ring is double bond.

TABLE 2

Structure of compound

Ar—Q—CH—N⟨piperidine⟩N—C(=O)—N—R₂ (benzimidazolinone)
      |
      R or

Ar—Q—CH—N=C(OR₃)—N (benzimidazole)
      |
      R

Abbreviations shown in tables have the following meaning.

Ac: CH₃CO—  Me: CH₃—  Et: C₂H₅—

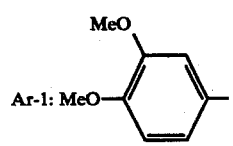
Ar-1:

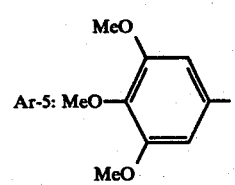
Ar-5:

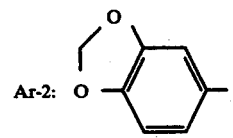
Ar-2:

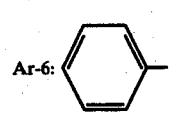
Ar-6:

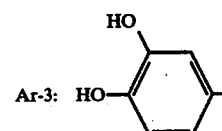
Ar-3:

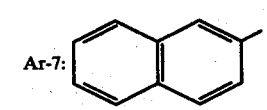
Ar-7:

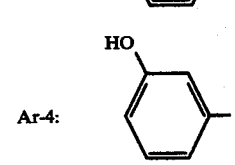
Ar-4:

| Compound No. | Structure | | | | |
|---|---|---|---|---|---|
| | Ar | Q | R | $R_2$ | $R_3$ |
| 1 | Ar-1 | —C(=O)— | H | H | — |
| 2 | Ar-2 | —C(=O)— | H | H | — |
| 3 | Ar-7 | —C(=O)— | H | H | — |
| 4 | Ar-1 | —C(=O)— | H | —C(=O)—Me | — |
| 5 | Ar-2 | —C(=O)— | H | — | Et |
| 6 | Ar-3 | —C(=O)— | H | H | — |
| 7 | Ar-2 | —CH(OH)— | H | H | — |
| 8 | Ar-1 | —CH(OH)— | H | H | — |
| 9 | Ar-3 | —CH(OH)— | H | H | — |
| 10 | Ar-7 | —CH(OH)— | H | H | — |
| 11 | Ar-2 | —CH(OH)— | H | — | Et |
| 12 | Ar-2 | —CH₂— | H | H | — |
| 13 | Ar-2 | —CH₂— | H | H | — |
| 14 | Ar-1 | —CH₂— | H | H | — |
| 15 | Ar-3 | —CH₂— | H | H | — |
| 16 | Ar-1 | —C(=O)— | CH₃ | H | — |
| 17 | Ar-2 | —C(=O)— | CH₃ | H | — |
| 18 | Ar-3 | —C(=O)— | CH₃ | H | — |
| 19 | Ar-2 | —CH(OH)— | CH₃ | H | — |
| 20 | Ar-3 | —CH(OH)— | CH₃ | H | — |
| 21 | Ar-4 | —CH(OH)— | CH₃ | H | — |
| 22 | Ar-1 | —CH(OH)— | CH₃ | H | — |
| 23 | Ar-2 | —CH(OAc)— | H | H | — |
| 24 | Ar-6 | —C(=O)— | H | H | — |
| 25 | Ar-6 | —CH(OH)— | H | H | — |
| 26 | Ar-2 | —C(=O)— | H | Et | — |
| 27 | Ar-2 | —CH(OH)— | H | Et | — |
| 28 | Ar-5 | —C(=O)— | H | H | — |
| 29 | Ar-5 | —CH(OH)— | H | H | — |
| 30 | Ar-5 | —C(=O)— | CH₃ | H | — |
| 31 | Ar-5 | —CH(OH)— | CH₃ | H | — |
| 32 | Ar-1 | —CH(OAc)— | CH₃ | Ac | — |

-continued

| Compound No. | Structure | | | | |
|---|---|---|---|---|---|
| | Ar | Q | R | $R_2$ | $R_3$ |
| 33 | Ar-1 | —CH—<br>\|<br>OH | $CH_3$ | Ac | — |
| 34 | Ar-1 | —CH—<br>\|<br>OAc | $CH_3$ | H | — |
| 35 | Ar-1 | —C—<br>\|\|<br>O | H | $COOC_2H_5$ | — |

Table 3 Properties (Melting point, IR, NMR and Elemental analysis)

(1) Form means the state of a compound subjected to the determination of properties.
  Blank: free base
  HCl: hydrochloride
  HBr: hydrobromide
(2) Values in the column of infrared absorption spectrum (IR) show characteristic maximum absorption of the compounds measured in KBr tablet.
(3) Values in the table of nuclear magnetic resonance spectrum (NMR) are δ values based on TMS in $d_6$-dimethylformamide (Compound Nos. 1 and 7), $d_6$-dimethylsulfoxide (Compound Nos. 28–31, 34 and 35) and $CDCl_3$ (Compound Nos. 32 and 33). (4) Asterisk (*) in the column of melting point shows decomposing point.
(5) Elemental analysis
  A: Calculated
  F: Found

TABLE 3-1

| Compound No. | Physicochemical properties (m.p., IR) | | |
|---|---|---|---|
| | Form | m.p. °C. | IR (cm$^{-1}$) |
| 1 | HCl | 178–179 | 1710–1680 |
| 2 | | 194–196 | 1700–1680, 1260 |
| 3 | | 175–177 | 1690, 1695 |
| 4 | | 157–159 | 1740, 1730, 1680 |
| 5 | | 135.5–137 | 1690, 1540, 1255 |
| 6 | HBr | 260–263* | 1685, 1695 |
| 7 | | 249–251 | 1700 |
| 8 | HCl, ½ H$_2$O | 180–183 | 1700 |
| 9 | HCl | | 1700–1680 |
| 10 | | 222–223.5 | 1702 |
| 11 | | 124–125 | 1545 |
| 12 | | 191.5–193.5 | 1710 |
| 13 | HCl | 240–245 | 1700 |
| 14 | | 155–157 | 1700 |
| 15 | HBr, 1.5 H$_2$O | 202–205* | 1690–1680 |
| 16 | | 178–180 | 1702, 1678 |
| 17 | | 150–160* | 1710, 1690 |
| 18 | HBr, ½ H$_2$O | 193–196 | 1690 |
| 19 | | 241–245* | 1699 |
| 20 | HCl, ½ H$_2$O | 187–189 | 1680 |
| 21 | HCl | 182–185 | — |
| 22 | | 210–211 | 1700 |
| 23 | Oil | — | 1740, 1700 |
| 24 | | 175–177 | 1705, 1695 |
| 25 | | 205–206 | 1700 |
| 26 | | 145–148 | 1700, 1685 |
| 27 | | 152–155 | 1700 |
| 28 | | 145–147 | 1700, 1690 |
| 29 | | 207–208.5 | 1700 |
| 30 | | 168–170 | 1700, 1690 |
| 31 | | 215–216 | 1700 |
| 32 | | 165–166 | 1735, 1720, 1709 |
| 33 | | 193–194.5 | 1730, 1710 |
| 34 | | 208–209 | 1730–1720 |

TABLE 3-1-continued

| Compound No. | Physicochemical properties (m.p., IR) | | |
|---|---|---|---|
| | Form | m.p. °C. | IR (cm$^{-1}$) |
| 35 | | 137–138 | 1790, 1715, 1692 |

TABLE 3-2

| Compound No. | Physicochemical properties (NMR) |
|---|---|
| | NMR (ppm) |
| 1 | 1.2–3.6, 3.85, 3.87, 3.9–4.6, 6.8–7.9, 10.75–11.0 |
| 7 | 1.35–3.6, 3.6–4.4, 4.4–5.3, 6.0 |
| 28 | 1.4–2.0, 2.0–2.63, 2.7–3.3, 3.4, 3.8, 3.9, 4.0–4.5, 6.8–7.5, 10.8 |
| 29 | 1.4–2.0, 2.0–2.7, 2.7–3.3, 3.7, 3.8, 4.0–4.4, 4.4–5.15, 6.6–7.4, 10.75 |
| 30 | 1.1, 1.4–2.0, 2.0–3.43, 3.8, 3.9, 4.0–4.6, 6.7–7.0, 10.75 |
| 31 | 0.75, 1.4–2.0, 2.0–3.4, 3.7, 3.8, 4.0–4.48, 5.0, 6.5–7.6, 10.88 |
| 32 | 2.2, 2.78 |
| 33 | 2.75 |
| 34 | 2.13 |
| 35 | 1.37, 4.43 |

TABLE 3-3

Physicochemical properties (Elemental analysis)
A: Calculated
F: Found

| Compound No. | Rational formula | | Elemental analysis (%) | | |
|---|---|---|---|---|---|
| | | | C | H | N |
| 1 | C$_{22}$H$_{26}$ClN$_3$O$_4$ | A | 61.18 | 6.07 | 9.73 |
| | | F | 61.07 | 6.23 | 9.51 |
| 2 | C$_{21}$H$_{21}$N$_3$O$_4$ | A | 66.48 | 5.58 | 11.08 |
| | | F | 66.60 | 5.52 | 11.01 |
| 3 | C$_{24}$H$_{23}$N$_3$O$_2$ | A | 74.78 | 6.01 | 10.90 |
| | | F | 74.71 | 6.23 | 11.02 |
| 4 | C$_{24}$H$_{27}$N$_3$O$_5$ | A | 65.89 | 6.22 | 9.61 |
| | | F | 65.77 | 6.42 | 9.59 |
| 5 | C$_{23}$H$_{25}$N$_3$O$_4$ | A | 67.79 | 6.18 | 10.31 |
| | | F | 67.80 | 6.23 | 10.27 |
| 6 | C$_{20}$H$_{22}$BrN$_3$O$_4$ | A | 53.58 | 4.95 | 9.37 |
| | | F | 53.30 | 5.00 | 9.11 |
| 7 | C$_{21}$H$_{23}$N$_3$O$_4$ | A | 66.12 | 6.08 | 11.02 |
| | | F | 66.06 | 6.04 | 10.98 |
| 8 | C$_{22}$H$_{28}$ClN$_3$O$_4$·½ H$_2$O | A | 59.66 | 6.60 | 9.49 |
| | | F | 59.44 | 6.63 | 9.26 |
| 9 | C$_{20}$H$_{24}$ClN$_3$O$_4$ | A | 59.19 | 5.96 | 10.35 |
| | | F | 59.36 | 6.21 | 10.33 |
| 10 | C$_{24}$H$_{25}$N$_3$O$_2$ | A | 74.39 | 6.50 | 10.85 |
| | | F | 74.56 | 6.56 | 10.78 |
| 11 | C$_{23}$H$_{27}$N$_3$O$_4$ | A | 67.46 | 6.65 | 10.26 |
| | | F | 67.75 | 6.88 | 10.21 |
| 12 | C$_{21}$H$_{21}$N$_3$O$_3$ | A | 69.40 | 5.83 | 11.56 |
| | | F | 69.35 | 5.93 | 11.50 |
| 13 | C$_{21}$H$_{24}$ClN$_3$O$_3$ | A | 62.76 | 6.02 | 10.46 |
| | | F | 62.71 | 5.99 | 10.38 |
| 14 | C$_{22}$H$_{27}$N$_3$O$_3$ | A | 69.27 | 7.13 | 11.02 |
| | | F | 69.21 | 7.02 | 11.41 |
| 15 | C$_{20}$H$_{24}$N$_3$O$_3$Br·1.5 H$_2$O | A | 52.07 | 5.90 | 9.11 |
| | | F | 52.42 | 5.89 | 9.11 |
| 16 | C$_{23}$H$_{27}$N$_3$O$_4$ | A | 67.46 | 6.65 | 10.26 |
| | | F | 67.23 | 6.65 | 10.20 |
| 17 | C$_{22}$H$_{23}$N$_3$O$_4$ | A | 67.16 | 5.89 | 10.68 |
| | | F | 67.44 | 5.91 | 10.61 |
| 18 | C$_{21}$H$_{25}$BrN$_3$O$_4$·½ H$_2$O | A | 53.51 | 5.35 | 8.91 |
| | | F | 53.65 | 5.51 | 9.04 |
| 19 | C$_{22}$H$_{25}$N$_3$O$_4$ | A | 66.82 | 6.37 | 10.63 |
| | | F | 66.78 | 6.32 | 10.55 |
| 20 | C$_{21}$H$_{26}$ClN$_3$O$_4$·½ H$_2$O | A | 58.81 | 6.35 | 9.80 |
| | | F | 58.81 | 6.45 | 9.79 |
| 21 | C$_{21}$H$_{26}$ClN$_3$O$_3$ | A | 62.45 | 6.49 | 10.40 |
| | | F | 62.53 | 6.21 | 10.77 |
| 22 | C$_{23}$H$_{29}$N$_3$O$_4$ | A | 67.13 | 7.10 | 10.21 |
| | | F | 67.00 | 7.15 | 10.22 |

TABLE 3-3-continued

Physicochemical properties
(Elemental analysis)
A: Calculated
F: Found

| Compound No. | Rational formula | | C | H | N |
|---|---|---|---|---|---|
| 23 | $C_{23}H_{25}N_3O_5$ | A | 65.23 | 5.95 | 9.92 |
| | | F | 65.20 | 6.11 | 9.91 |
| 24 | $C_{20}H_{21}N_3O_2$ | A | 71.62 | 6.31 | 12.53 |
| | | F | 71.55 | 6.37 | 12.52 |
| 25 | $C_{20}H_{23}N_3O_2$ | A | 71.19 | 6.87 | 12.45 |
| | | F | 71.22 | 7.01 | 12.42 |
| 26 | $C_{23}H_{25}N_3O_4$ | A | 67.79 | 6.18 | 10.31 |
| | | F | 67.82 | 6.27 | 10.30 |
| 27 | $C_{23}H_{27}N_3O_4$ | A | 67.46 | 6.65 | 10.26 |
| | | F | 67.55 | 6.73 | 10.24 |
| 28 | $C_{23}H_{27}N_3O_5$ | A | 64.92 | 6.40 | 9.88 |
| | | F | 64.73 | 6.51 | 9.65 |
| 29 | $C_{23}H_{29}N_3O_5$ | A | 64.62 | 6.84 | 9.83 |
| | | F | 64.45 | 6.94 | 9.76 |
| 30 | $C_{24}H_{29}N_3O_5$ | A | 65.58 | 6.65 | 9.56 |
| | | F | 65.67 | 6.74 | 9.56 |
| 31 | $C_{24}H_{31}N_3O_5$ | A | 65.28 | 7.08 | 9.52 |
| | | F | 65.01 | 7.08 | 9.41 |
| 32 | $C_{27}H_{33}N_3O_5$ | A | 65.44 | 6.71 | 8.48 |
| | | F | 65.34 | 6.78 | 8.33 |
| 33 | $C_{25}H_{31}N_3O_5$ | A | 66.20 | 6.89 | 9.27 |
| | | F | 66.08 | 6.99 | 9.27 |
| 34 | $C_{25}H_{31}N_3O_5$ | A | 66.20 | 6.89 | 9.27 |
| | | F | 66.06 | 6.87 | 9.14 |
| 35 | $C_{29}H_{35}N_3O_{10}$ | A | 55.48 | 6.03 | 7.18 |
| | | F | 55.42 | 6.01 | 7.42 |

Acute toxicity and hypotensive action of the compounds of the present invention are shown below as experiments.

Experiment 1 Acute toxicity

Three male dd-strain mice (weight 20±1 g) were used for each test compound.

Each of the compounds shown in Table 4 was dissolved or suspended in a physiological saline, and the resulting solution or suspension was administered to the mice intraperitoneally (i.p.) in a dose of 200 mg/kg or orally (p.o.) in a dose of 1000 mg/kg. After the observation for 7 days, the numbers of deaths were counted, and the results are shown in Table 4.

Table 4 also shows the data on hypotensive activity of the test compounds on rats (Experiment 3).

TABLE 4

BP: Reduction of blood pressure
++: Blood pressure was reduced by 11% or more.
+: Blood pressure was reduced by 6–10%.

| Compound Number | Number of Death | | BP |
|---|---|---|---|
| | I.P. | P.O. | |
| 1 | 0 | 0 | ++ |
| 2 | 0 | 0 | + |
| 4 | 0 | 0 | + |
| 6 | 0 | 0 | + |
| 7 | 0 | 0 | ++ |
| 8 | 0 | 0 | ++ |
| 9 | 0 | 0 | ++ |
| 10 | 0 | 0 | + |
| 11 | 0 | 0 | + |
| 12 | 0 | 0 | + |
| 14 | 0 | 0 | ++ |
| 15 | 0 | 0 | + |
| 16 | 0 | 0 | ++ |
| 17 | 0 | 0 | + |
| 18 | 0 | 0 | + |
| 19 | 0 | 0 | + |
| 20 | 0 | 0 | + |
| 21 | 0 | 0 | + |
| 22 | 0 | 0 | ++ |
| 25 | 0 | 0 | ++ |
| 27 | 0 | 0 | + |
| 28 | 0 | 0 | ++ |
| 29 | 0 | 0 | ++ |
| 30 | 0 | 0 | ++ |
| 31 | 0 | 0 | ++ |
| 32 | 0 | 0 | ++ |
| 33 | 0 | 0 | ++ |
| 34 | 0 | 0 | ++ |
| 35 | 0 | 0 | ++ |

Experiment 2 Acute toxicity ($LD_{50}$)

Ten male dd-strain mice (weight 20±1 g) were used as one group.

Each of the compounds shown in Table 5 was dissolved or suspended in a physiological saline, and the resulting solution or suspension was administered to the mice intraperitoneally, subcutaneously or orally. The $LD_{50}$ was calculated from the death rate obtained after the observation for 7 days according to the method of Litchfield and Wilcoxon [J. Pharmacol. Exper. Therap., 96, 99 (1949)].

TABLE 5

| Compound No. | $LD_{50}$ (mg/kg) | | |
|---|---|---|---|
| | Intraperitoneal administration | Subcutaneous administration | Oral administration |
| 1 | 485 | >3000 | >6000 |
| 7 | 500 | >1000 | 1500 |
| 9 | 800 | >1000 | 3000 |
| 20 | 1500 | >3000 | >6000 |
| 21 | 500 | >1000 | 2500 |

Experiment 3 Hypotensive action

This experiment was conducted according to the method described in Proc. Soc. Exp. Biol. MED vol. 104, 25937 (1960).

Three males Wistar-strain rats (weight 200–300 g) were used for each test compound. A cannula for measuring blood pressure was inserted into the left common carotid of each rat. Each of the compounds shown in Table 4 was dissolved in 0.3% (w/v) CMC (carboxymethylcellulose) sodium salt aqueous solution in a concentration of 5 mg/ml. The resulting solution was orally administered to said rats in an amount of 1 ml (5 mg as the test compound) per 100 g of the rat weight, and the maximum reduction in blood pressure after the administration was measured. The results are shown in Table 4.

Experiment 4 Hypotensive action measured by observation of blood

This experiment was conducted according to the method described in "Evaluation of Medical Effects (1), Pharmacological Tests (II) (Basic Lectures on Development of Medicines V)" compiled by Kyosuke Tsuda, et al. and published by Chijin Shokan (Oct. 10, 1971) pp. 464–468.

Six male Wistar-strain rats (weight 250–320 g) were used as one group. Each rat was anesthetized by intraperitoneal administration of 600 mg/kg of urethane and 60 mg/kg of α-chloralose. A cannula was inserted into the left common carotid of each rat, and the blood pressure was recorded on an ink oscillography through a transducer.

Then, Tween 80 [trade name of a nonionic surface active agent produced by Atlas Powder Co. (U.S.A.); fatty acid ester of polyoxyethylenesorbitan] was added to each of the compounds shown in Table 6 in an amount of one drop per about 30 mg of the test compound. Each of the resulting mixtures was suspended in 15% (w/v) physiological saline suspension of gum arabic in a concentration of 15 mg/ml, and the suspension was intraperitoneally administered to the rats in a dose of 0.2 mg/100 g (30 mg/kg as the test compound). Table 6 shows changes in blood pressure (mmHg) with the passage of time indicated, on the basis of the pressure immediately before the administration (expressed as 0) (the value is the average of the results on the six rats).

TABLE 6

| Compound No. | Immediately before the administration | Time passed after the administration | | | | | |
|---|---|---|---|---|---|---|---|
| | | 10 min. | 30 min. | 1 hr. | 2 hrs. | 3 hrs. | 4 hrs. |
| 1 | 0 | −23 | −44 | −50 | −56 | −54 | −51 |
| 7 | 0 | −58 | −40 | −42 | −36 | −26 | −18 |
| 9 | 0 | −67 | −75 | −76 | −69 | −64 | −63 |
| 20 | 0 | −58 | −65 | −65 | −57 | −44 | −34 |
| 21 | 0 | | −48 | −47 | −39 | −42 | −48 |

Experiment 5 Changes in blood pressure due to continuous administration

This experiment was conducted according to the method described in "Spontaneously Hypertensive Rats (SHR): Guidelines for Breeding, Care and Use" (published by SHR Conference) (1976) p. 11.

Five spontaneously hypertensive rats (11 weeks old) and five DOCA (deoxycorticosterone acetate)-sodium chloride loaded hypertensive rats (a kind of artificially hypertensive rat) (having been bred for 5 weeks after removing one kidney) were respectively used as one group.

Compound 1 was dissolved in 0.3% (w/v) CMC aqueous solution in a concentration of 3 mg/ml. The resulting solution was orally administered to the rats once a day in a dose of 1 ml/100 g (30 mg/kg as the compound) for 9 consecutive days.

Changes in blood pressure (mmHg) during the period of from immediately before the administration to the 9th day of the administration were measured according to the method of tail artery plethysmography (see the literature cited above). The results are shown in Table 7 (the value is the average of the results on the five rats).

TABLE 7

| Kind of rats | Immediately before the administration | Time passed after the administration | | |
|---|---|---|---|---|
| | | 1st day | 4th day | 9th day |
| Spontaneously hypertensive rats | 197 | 158 | 160 | 140 |
| DOCA—NaCl loaded hypertensive rats | 185 | 140 | 140 | 144 |

Experiment 6 Dosage-reaction curve: compared with betanidin

Five spontaneously hypertensive rats (16 weeks old) and five DOCA-sodium chloride loaded hypertensive rats (having been bred for 5 weeks after removing one kidney) were respectively used as one group.

As the test compounds, Compound 1 and betanidin sulfate, which is a known hypotensive agent, were used.

The test compounds were respectively dissolved in 0.3% (w/v) CMC aqueous solution and each of the resulting solutions was orally administered to the rats in a dose of 1 ml/100 g. The amounts of the solutions administered were equal per unit weight of rats and the concentrations thereof were varied according to the doses of the compounds indicated in Table 8. The maximum reduction in blood pressure after the administration was measured according to the method of tail artery plethysmography. Table 8 shows the maximum reduction in blood pressure (mmHg) for each dose on the basis of the pressure immediately before the administration (expressed as 0) (the value is the average of the results on the five rats).

TABLE 8

| Test compound | Rats | Dose (mg/kg) | | | | |
|---|---|---|---|---|---|---|
| | | 0.1 | 0.5 | 1.0 | 10 | 50 |
| Compound I | Spontaneously hypertensive rats | — | −29 | −34 | −50 | −57 |
| Betanidin sulfate | Spontaneously hypertensive rats | —−17 | — | — | −40 | |
| Compound I | DOCA—NaCl loaded hypertensive rats | −12 | — | −29 | −46 | −72 |
| Betanidin sulfate | DOCA—NaCl loaded hypertensive rats | — | — | −25 | −34 | −58 |

The processes for preparing the compounds represented by the general formula (I) classified by the kind of group Q are described below.

(1) Process for preparing the compounds represented by the general formula (I) wherein Q is

The compounds are prepared by the reaction illustrated by the following reaction formula.

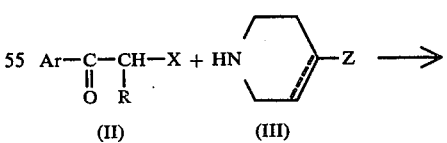

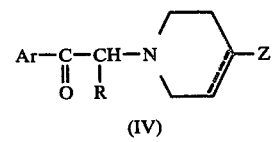

(wherein Ar, R and Z have the same significance as defined above and X represents a halogen such as Cl and Br,

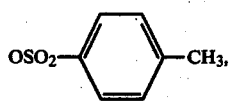

OSO$_2$CH$_3$, etc.)

The above reaction is carried out in an inert solvent in the presence of a base. As the base, organic bases such as triethylamine, lower alkoxides of metals such as sodium methoxide and sodium ethoxide, and inorganic bases such as sodium hydroxide, potassium hydroxide and potassium carbonate may be used. The amount of the base is 1.0–1.2 times the equivalent amount based on the starting compounds. The two starting compounds are usually used in equimolar amounts.

As the inert solvent, those which do not participate in the reaction such as chloroform, dichloromethane, dimethylformamide, benzene, toluene, tetrahydrofuran, methanol, ethanol and isopropanol are used. The reaction is usually carried out at 0°–80° C. and is completed in 0.5–24 hours.

When Ar is a substituted phenyl group having a hydroxyl group as a substituent, the hydroxyl group in Compound II is generally protected with a protecting group in advance. After the completion of reaction, the protecting group is removed by a conventional method to obtain the desired compound.

(2) Process for preparing the compounds represented by the general formula (I) wherein Q is

The compounds are prepared by reducing the compounds of the general formula (IV)

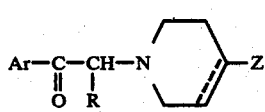

(wherein Ar, R and Z have the same significance as defined above) obtained in the above (1).

Reduction is conducted, for example, by treatment with metallic sodium in a solvent such as methanol, ethanol, etc., by treatment with lithium aluminum hydride, sodium boron hydride, etc., or by catalytic reduction in the presence of hydrogen and catalysts such as platinum, palladiumcarbon, nickel, copper, etc. These reductions are preferably carried out at 0°–80° C. in the presence of a diluent or solvent in an open or closed vessel under pressure. The reducing agents and catalysts are properly selected according to the kinds of Ar, Z and R and the substituents.

(3) Process for preparing the compounds represented by the general formula (I) wherein Q is

(wherein R$_1$ has the same significance as defined above provided that R$_1$ is not H)

The compounds are obtained by acylating or alkylating the compounds of the general formula (V)

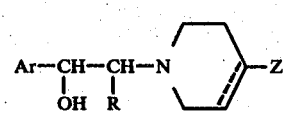

(wherein Ar, R and Z have the same significance as defined above) obtained in the above (2)

(3-1) Acylation

The desired compound is obtained by reacting Compound (V) with an acylating agent in an inert solvent.

As the acylating agent, carboxylic acid corresponding to group R$_1$, acid halides of the carboxylic acid such as acid chloride, acid bromide, etc., acid anhydrides (pure or mixed acid anhydrides), and intramolecular anhydrides (e.g., ketene) may be used.

As the inert solvent, chloroform, dichloromethane, dimethylformamide, tetrahydrofuran, etc., may be used.

The above reaction is preferably carried out in the presence of an organic or inorganic base such as triethylamine, sodium hydride, 4-dimethylaminopyridine, etc.

The amount of the acylating agent is 1.0–1.1 times the equivalent amount based on Compound (V). Reaction is carried out at 0° C.-room temperature and is completed in 1–24 hours.

(3-2) Alkylation

Alkylation is carried out according to the following reaction formula:

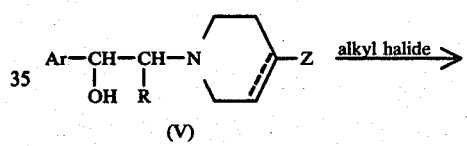

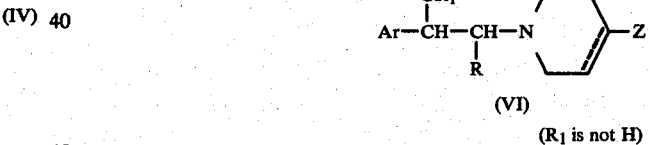

(R$_1$ is not H)

Alkylation is carried out by reacting Compound (V) with an alkyl halide in an inert solvent in the presence of a base at room temperature $-100°$ C.

Examples of the alkyl halide are alkyl iodide, alkyl chloride and alkyl bromide. As the base, sodium hydride, potassium hydride, sodium methylate, sodium ethylate, triethylamine, etc. may be used.

As the inert solvent, chloroform, dimethylformamide, dichloromethane, etc. may be used.

The amounts of the alkyl halide and the base are 1.0–1.1 times the equivalent amount based on Compound (V).

(4) Process for preparing the compounds represented by the general formula (I) wherein Q is —CH$_2$—

The compounds can be prepared by catalytically hydrogenating Compound (IV) or Compound (V), or by reacting Compound (IV) or Compound (V) with a silicon compound.

(4-1) Catalytic hydrogenation

Reaction is carried out in an inert solvent in the presence of a catalyst and hydrogen at room temperature $-100°$ C.

Preferably, the reaction is carried out under acidic condition, for example, in the presence of sulfuric acid or hydrochloric acid (Ann., 565, 51, 1949). As the catalyst, palladium carbon, Raney nickel, etc. are usually used in an amount of 1–10% (w/w) based on the starting compound.

As the inert solvent, methanol, ethanol, dioxane, etc. may be used.

(4-2) Hydrogenation using a silicon compound

Hydrogenation is carried out by reacting the starting compound with a silicon compound such as trialkylsilane or alkylarylsilane in the presence of a Lewis acid such as boron fluoride or aluminum chloride, an organic acid such as trifluoroacetic acid or acetic acid, or an inorganic acid such as hydrochloric acid, sulfuric acid or hydrobromic acid at 0–50° C. Though trifluoroacetic acid, acetic acid, etc. also function as a solvent, the reaction may be carried out in an inert solvent such as chloroform, dichloromethane, etc. The silicon compound and the acid are used in amounts of 2–10 mols per one mol of the starting compound.

In addition to the above-described processes, the desired compounds of the present invention can be prepared by the following processes.

(5) Among the compounds of the general formula (I), those represented by the general formula (VII)

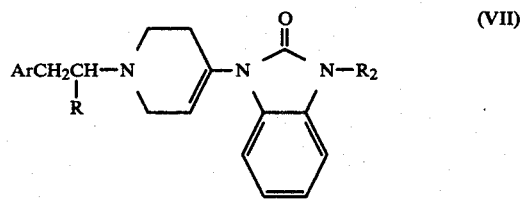

(wherein Ar and R have the same significance as defined above) can be prepared according to the process shown by the following reaction formulae:

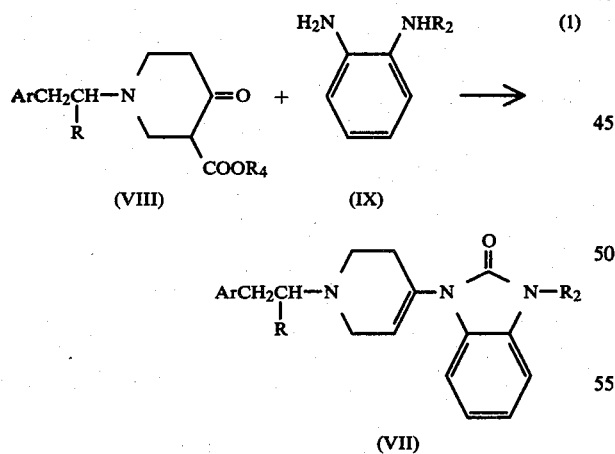

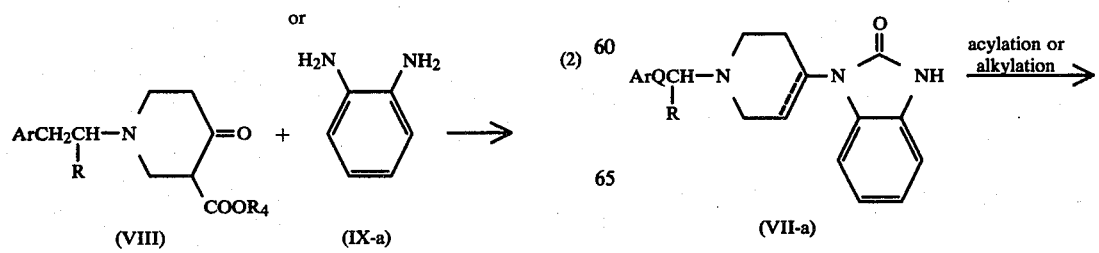

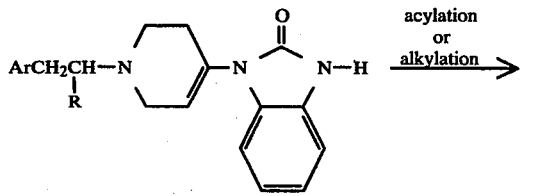

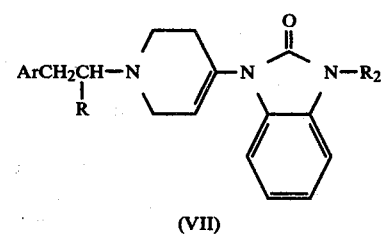

(wherein $R_4$ represents a lower alkyl group such as methyl or ethyl, and Ar, R and $R_2$ have the same significance as defined above).

The above reaction (1) and the first step of reaction (2) can be carried out according to the processes described in Helv. Chim. Acta. 163, 1298 (1960) and Tetrahedron Lett., 46, 4811 (1968). In both reactions, the starting compounds are used in equimolar amounts. These reactions are generally carried out in an inert high-boiling solvent such as xylene, toluene, glyme, dimethylformamide, ect. at 60°–160° C.

The second step of the above reaction (2) can be carried out under the same conditions as in the acylation and alkylation of the above (3).

(6) The compounds represented by the general formula (I) wherein Z is

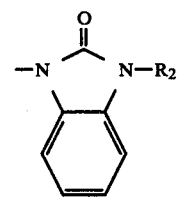

can be prepared by the reaction shown by the following reaction formula:

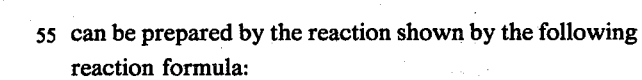

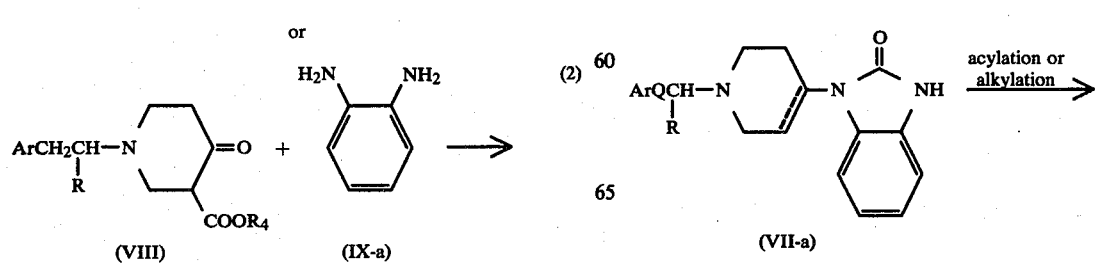

-continued

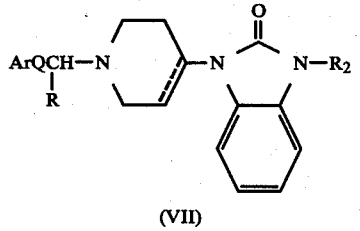

(VII)

(wherein Ar, Q, R and $R_2$ have the same significance as defined above).

When Q is CH(OH), introduction of $R_2$ into the 3-position of the benzimidazolinyl group simultaneously causes conversion of Q from CH(OH) to CH(OR$_2$). (In this case, $R_1$ naturally becomes equal to $R_2$.) When Q is CH(OR$_1$), $R_1$ and $R_2$ may be made the same or different. This reaction can be carried out under the same conditions as in the acylation and alkylation of the above (3).

(7) The compounds represented by the general formula (I) wherein Z is

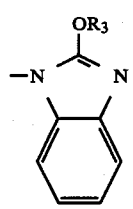

can be prepared by the reaction shown by the following reaction formula:

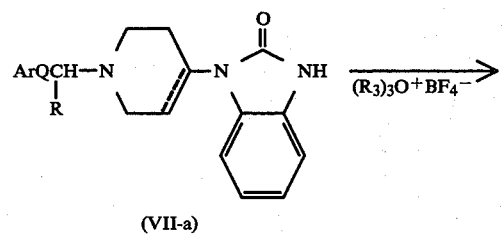

(wherein Ar, Q, R and $R_3$ have the same significance as defined above).

When Q is CH(OH), alkylation of the keto group at the 2-position of the benzimidazolinyl group simultaneously converts Q from CH(OH) to CH(OR$_3$). (In this case, $R_1$ naturally becomes equal to $R_3$.) When Q is CH(OR$_1$), $R_1$ and $R_3$ may be made the same or different. The compound represented by $(R_3)_3O^+BF^-_4$ is usually used in an equimolar amount [double the molar amount when Q is CH(OH)] based on the starting compound.

Reaction is carried out in a solvent which does not participate in the reaction, for example, chloroform, methylene chloride, benzene and tetrahydrofuran, at a temperature of 0°–50° C.

Isolation and purification of the desired compounds are carried out according to conventional methods such as concentration, extraction, recrystallization, chromatography, etc.

Specifically, as the desired compounds readily crystallize in general, they can be isolated and purified by distilling off the reaction solvent after completion of the aforesaid reactions (1)–(7) and recrystallizing the residue from a suitable solvent. The compounds which are oily in a free state can be crystallized in the form of various acid addition salts. Further, the compounds which do not crystallize even in the form of acid addition salts can be purified by chromatography using silica gel, alumina, etc.

The starting compounds used in the above processes are described below.

(i) A process for preparing the compounds represented by the general formula

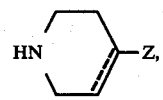

which are the starting compounds in the above-stated process (1), is described below.

The compounds of the above formula wherein Z is

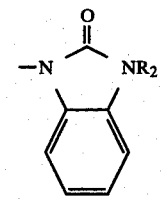

(wherein $R_2$ has the same significance as defined above) are known and the process for preparing them is disclosed in Japanese Published Unexamined Patent Application No. 13780/76.

The compounds of the above formula wherein Z is

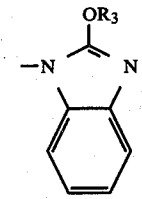

(wherein $R_3$ has the same significance as defined above) can be prepared by the reaction illustrated below:

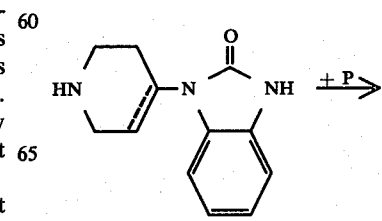

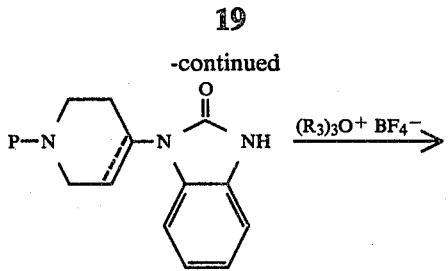

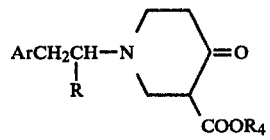

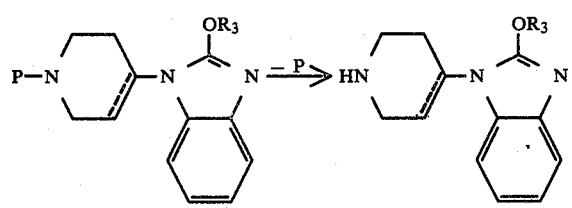

(wherein P represents a protecting group for the nitrogen atom in the piperidine ring described below and $R_3$ has the same significance as defined above).

The nitrogen atom in the piperidine ring is usually protected with a protecting group P prior to the alkylation of the keto group at the 2-position of the benzimidazolinyl group. As the protecting group P, those which can be eliminated under mild conditions are preferred. Examples of the preferred protecting groups are benzyl, benzyloxycarbonyl, t-butyloxycarbonyl and trifluoroacetyl. The thus obtained (2-keto-1-benzimidazolinyl)-piperidine derivatives wherein the nitrogen atom in the piperidine ring is protected are then reacted with a Meerwein reagent (trialkyloxonium fluoroborate) to obtain the derivatives wherein the keto group at the 2-position of the benzimidazolinyl group is alkylated. The Meerwein reagent is usually used in an equimolar amount based on the starting compound. Reaction is carried out in a solvent which does not participate in the reaction such as chloroform, dichloromethane, tetrahydrofuran, benzene, toluene, etc. at a temperature of 0°–50° C.

(ii) Many of Compounds (II) which are the starting compounds in the above-stated process (1) are known in literature [J. Ame. Chem. Soc., 77, 2896 (1955), Farmaco Ed. Sci., 22, 667 (1967), J. Med. Chem., 18, 674 (1975), J. Med. Chem., 20, 394 (1977), etc.] and processes for synthesizing them are disclosed in the literature. A few unknown compounds can also be readily synthesized according to the processes disclosed in the above-mentioned literature.

(iii) Compounds (VIII) which are the starting compounds in the above-stated process (5) can be prepared according to the following process.

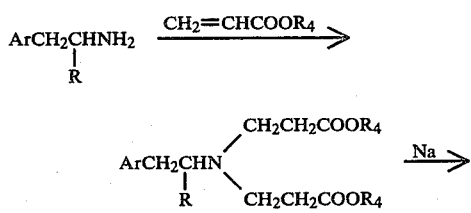

The first step of the above reaction is carried out according to the process described in Bull. Chem. Soc. Jap., 31, 418 (1958). The compound represented by $CH_2{=}CHCOOR_4$ is used in an amount of 2–10 mols per one mol of the starting compound. This compound usually also functions as a solvent, but an inert solvent such as ethanol may be used. Reaction is carried out under reflux at the boiling point of the solvent and is completed in 12–40 hours.

The second step of the above reaction can be carried out according to the process described in J. Am. Chem. Soc., 49, 2862 (1927) and J. Heterocyclic Chem., 2, 326 (1965).

That is, the starting compounds (diesters) obtained in the first step are reacted with sodium, sodium hydride or sodium ethoxide in an inert organic solvent such as xylene, toluene, etc. Reaction is carried out by suspending 1.1–1.2 mols of sodium hydride or the like per one mol of the starting compound in an inert solvent, adding a solution of the starting compound in an inert solvent by portions to the suspension at a temperature of room temperature to 40° C., and then refluxing the mixture at the boiling point of the solvent.

Isolation and purification of the formed starting compounds are carried out in the same manner as in the isolation and purification of the compounds of the general formula (I) described above.

In order to obtain the desired compound as an acid addition salt, the corresponding acid is reacted with a free base in a suitable solvent. Hydrochloride can be obtained by introducing hydrogen chloride gas into the solvent containing a free base. Further, conventional methods for preparing acid addition salts can be applied.

The pharmaceutical compositions of the present invention are described below.

It is obvious from the foregoing various experimental data that the compounds of the general formula (I) have a hypotensive action.

In view of the hypotensive action, the compounds of the present invention may be used in various pharmaceutical forms for administration. Pharmaceutical compositions of the present invention are prepared by uniformly mixing an effective amount of the compound in the form of a base or a acid addition salt as an active ingredient with a pharmaceutically acceptable carrier. According to the pharmaceutical forms suitable for administration, the carrier may take various forms. It is desirable that the pharmaceutical compositions are in single administration form suitable for administration per os or by injection.

In preparation of the compositions for oral administration, any useful pharmaceutical carrier may be used. For example, water, glycols, oils, alcohols, etc. may be used to prepare oral liquid preparations such as suspensions and syrups, and excipients, lubricants, binders, disintegrators, etc. may be used to prepare powders, pills, capsules and tablets. Examples of the carriers are glucose and lactose as the excipients, starch and sodium alginate as the disintegrators, magnesium stearate, paraffin sulfate and talc as the lubricants, and syrup, ethanol and gelatin as the binders. The active ingredient is administered in a dose of 1–100 mg per day for an adult, and particularly, 10–60 mg per os.

BEST MODE OF CARRYING OUT THE INVENTION

Certain specific embodiments of the invention are illustrated by the following representative examples.

Example 1

To a solution comprising 1.52 g of 4-(2-keto-1-benzimidazolinyl)-piperidine, 0.74 g of triethylamine, and 20 ml of chloroform is added 1.84 g of 3,4-dimethoxy-α-bromoacetophenone. The reaction is carried out for 6 hours at 35° C. with stirring. As post-treatment of the reaction, the solvent is distilled away under reduced pressure. Water is added to the residue, and, after stirring, the mixture is subjected to filtration. Crystals collected are washed with water and then with ethanol, followed by drying. Thus, there is obtained 2.46 g of crude crystals. In order to obtain the desired compound as hydrochloride, the resulting crude crystals are suspended in 20 ml of methanol, and a solution comprising 0.24 g of dry hydrogen chloride and 5 ml of methanol is added thereto. The thus obtained solution is concentrated under reduced pressure. After adding ethyl acetate to the residue, the mixture is filtered and dried to obtain 2.4 g of a hydrochloride. Recrystallization of this product from ethanol yields 2.16 g of 1-[2-oxo-2-(3,4-dimethoxyphenyl)-1-ethyl]-4-(2-keto-1-benzimidazolinyl)-piperidine hydrochloride.

Example 2

To a solution comprising 3.35 g of 4-(2-keto-1-benzimidazolinyl)-piperidine, 1.6 g of triethylamine, and 60 ml of dichloromethane is added 3.75 g of 3,4-methylenedioxy-α-bromoacetophenone. After stirring the solution for 6 hours at 30° C., the solvent is distilled away under reduced pressure. Water is added to the residue and, after stirring, the mixture is subjected to filtration. Crystals thus obtained are washed with water, then with ethanol, and dried to obtain 4.4 g of crude crystals. Recrystallization of the crude crystals from methanol yields 3.7 g of 1-[2-oxo-2-(3,4-methylenedioxyphenyl)-1-ethyl]-4-(2-keto-1-benzimidazolinyl)-piperidine.

Example 3

To a solution comprising 3.0 g of 4-(2-keto-1-benzimidazolinyl)-piperidine, 1.5 g of triethylamine, and 40 ml of chloroform is added 3.5 g of α-bromo-2-acetonaphthone. The resulting solution is stirred for 3 hours at 35° C. The same post-treatment as in Example 1 is conducted to obtain 4.65 g of crude crystals. Recrystallization of the crystals from ethanol yields 3.73 g of 1-[2-oxo-2-(2-naphthyl)-1-ethyl]-4-(2-keto-1-benzimidazolinyl)-piperidine.

Example 4

To a solution comprising 1.5 g of 4-(2-keto-3-acetyl-1-benzimidazolinyl)-piperidine hydrochloride, 1.1 g of triethylamine, and 20 ml of chloroform is added 1.32 g of 3,4-dimethoxy-α-bromoacetophenone, and the mixture is stirred overnight at room temperature. The same post-treatment as in Example 1 is conducted to obtain 1.27 g of crude crystals. Recrystallization of the crystals from methanol yields 1.0 g of 1-[2-oxo-2-(3,4-dimethoxyphenyl)-1-ethyl]-4-(2-keto-3-acetyl-1-benzimidazolinyl)-piperidine.

Example 5

To a solution comprising 1.76 g of 4-(2-ethoxy-1-benzimidazolinyl)-piperidine, 730 mg of triethylamine, and 20 ml of chloroform is added 1.75 g of 3,4-methylenedioxy-α-bromoacetophenone. The resulting solution is stirred at 30° C. for 6 hours. The same post-treatment as in Example 1 is conducted to obtain 1.8 g of crude crystals. Recrystallization of the crystals from ethanol yields 1.5 g of 1-[2-oxo-2-(3,4-methylenedioxyphenyl)-1-ethyl]-4-(2-ethoxy-1-benzimidazolinyl)-piperidine.

4-(2-ethoxy-1-benzimidazolinyl)-piperidine used as a starting material in this reaction can be prepared as follows.

A solution comprising 0.5 g of 1-t-butyloxycarbonyl-4-(2-keto-1-benzimidazolinyl)-piperidine, 330 mg of triethoxonium fluoroborate, and 10 ml of methylene chloride is stirred at 25° C. for 25 hours. The resulting reaction solution is cooled to 0° C., and a cold 1 N sodium carbonate aqueous solution is added thereto to make the pH 9.5. The organic layer is washed several times with water, and dried. The solvent is distilled away to obtain 0.54 g of crystals. Recrystallization of the crystals from N-hexane yields 260 mg of 1-t-butyloxycarbonyl-4-(2-ethoxy-1-benzimidazolinyl)-piperidine.

m.p.: 107°–109° C.

IR absorption spectrum: 1690, 1680, 1540 cm$^{-1}$.

510 mg of 1-t-butyloxycarbonyl-4-(2-ethoxy-1-benzimidazolinyl)-piperidine obtained in the same manner as above is added to 1.68 g of trifluoroacetic acid cooled to 0° C. After stirring for 1.5 hours at the same temperature, trifluoroacetic acid is distilled away under reduced pressure. 3 ml of water is added to the residue to make a solution, and 400 mg of triethylamine is added thereto. Isolated oily product is extracted with chloroform, and the chloroform layer is washed with water, and dried. Chloroform is distilled away to obtain 280 mg of 4-(2-ethoxy-1-benzimidazolinyl)-piperidine as an oily product. When the product is subjected to chromatography using a lower layer of a mixture of chloroform/methanol/acetic acid/water (10/10/1/10) (by volume, hereinafter the same shall apply) as a developing solvent the product provides single spot at $R_f=0.31$. IR absorption spectrum: 1555, 1550 cm$^{-1}$. Although the product can be used as it is, it is converted to hydrochloride by adding equimolar hydrogen chloride in ethyl acetate for the subsequent reaction. The properties of the hydrochloride are as follows.

m.p.: 260°–270° C. (decomposition).

Elemental analysis: Calcd. for $C_{14}H_{20}ClN_3O$: C=59.67; H=7.15, N=14.91. Found: C=59.92; H=7.09; N=14.95.

Example 6

1-[2-oxo-2-(3,4-methylenedioxyphenyl)-1-ethyl]-4-(2-keto-1-benzimidazolinyl)-piperidine obtained in the same manner as in Example 2 is converted to a hydrochloride in methanol in the same manner as in Example 1. 2.3 g of the resulting hydrochloride is suspended in 20 ml of dry dichloromethane. The suspension is cooled to 0° C., and 4.2 g of boron tribromide is added thereto. The suspension is stirred overnight at room temperature, followed by filtration. The thus obtained powder is washed with chloroform. This powder is then poured into ice-water and, after well stirring, filtered. The resulting powder is washed with water, then with ethanol and dried to obtain 2.2 g of crude crystals. Recrystallization of the crystals from ethanol yields 2.0 g of 1-[2-oxo-2-(3,4-dihydroxyphenyl)-1-ethyl]-4-(2-keto-1-benzimidazolinyl)-piperidine hydrobromide.

Example 7

2.0 g of 1-[2-oxo-2-(3,4-methylenedioxyphenyl)-1-ethyl]-4-(2-keto-1-benzimidazolinyl)-piperidine obtained in the same manner as in Example 2 is suspended in 240 ml of methanol. 0.6 g of sodium borohydride is added by portions thereto over 30 minutes at room temperature. After the addition, the mixture is stirred at 40° C. for 2 hours. Then, the reaction solution is concentrated to 50 ml. 30 ml of water is added to the concentrate and, after stirring, the thus formed crystals are collected by filtration and then dried. Recrystallization of the crude crystals from methanol yields 1.8 g of 1-[2-hydroxy-2-(3,4-methylenedioxyphenyl)-1-ethyl]-4-(2-keto-1-benzimidazolinyl)-piperidine.

Example 8

1.3 g of 1-[2-oxo-2-(3,4-dimethoxyphenyl)-1-ethyl]-4-(2-keto-1-benzimidazolinyl)-piperidine crude crystals obtained in the same manner as in Example 1 are dissolved in 200 ml of dry tetrahydrofuran. The resulting solution is cooled to 0° C., and 0.5 g of lithium aluminum hydride is added by portions thereto. After the addition, the mixture is gradually heated to room temperature, and stirred for 1 hour at room temperature. The reaction mixture is then poured into ice-water. Chloroform is added to the mixture and, after well stirring, the mixture is filtered. The residue is washed with chloroform. The filtrate and washing liquid are combined, whereby two layers are formed. The chloroform layer is washed with water, dried and concentrated to obtain 1.52 g of crystals. The crystals are added to methanol and hydrogen chloride gas is bubbled into the mixture to convert the crystals to hydrochloride. Recrystallization of the hydrochloride from methanol/ethyl acetate yields 1.3 g of 1-[2-hydroxy-2-(3,4-dimethoxyphenyl)-1-ethyl]-4-(2-keto-1-benzimidazolinyl)-piperidine hydrochloride.

Example 9

2.31 g of 1-[2-hydroxy-2-(3,4-dibenzyloxyphenyl)-1-ethyl]-4-(2-keto-1-benzimidazolinyl)-piperidine hydrochloride is dissolved in 250 ml of methanol. 0.3 g of palladium carbon (10%) is added thereto, and the mixture is vigorously shaked in a hydrogen stream under atmospheric pressure. After discontinuation of the absorption of hydrogen, the catalyst is filtered off, and the mother liquor is concentrated. To the residual syrup is added ethyl acetate, and the mixture is well stirred. The mixture is filtered to obtain powdered product, and the product is washed with ethyl acetate and dried to obtain 1.52 g of 1-[2-hydroxy-2- (3,4-dihydroxyphenyl)-1-ethyl]-4-(2-keto-1-benzimidazolinyl)-piperidine hydrochloride as amorphous powder. When subjected to thin layer chromatography using a lower layer of a mixture of chloroform/methanol/acetic acid/water (10/10/1/10), this product provides single spot at $R_f$=0.15.

1-[2-hydroxy-2-(3,4-dibenzyloxyphenyl)-1-ethyl]-4-(2-keto-1-benzimidazolinyl)-piperidine hydrochloride used as a starting material in the above reaction is prepared as follows.

To a solution comprising 2.4 g of 4-(2-keto-1-benzimidazolinyl)-piperidine, 1.2 g of triethylamine, and 50 ml of dichloromethane is added 5.0 g of 3,4-dibenzyloxy-α-bromoacetophenone. The resulting solution is stirred overnight at 20° C., and subjected to the same post-treatment as in Example 1 to obtain 5.7 g of crude crystals. Recrystallization of the crystals from a mixed solvent of ethanol/ethyl acetate (2:3 by volume) yields 5.6 g of 1-[2-oxo-2-(3,4-dibenzyloxyphenyl)-1-ethyl]-4-(2-keto-1-benzimidazolinyl)-piperidine.

m.p.: 118°–120.5° C.

IR absorption spectrum: 1680, 1700 cm$^{-1}$.

Elemental analysis: Calcd. for $C_{34}H_{33}N_3O_4$: C=74.56; H=6.07; N=7.67. Found: C=74.23; H=6.41; N=7.66.

Then, 4.7 g of the thus obtained product is suspended in 200 ml of methanol. 2 g of sodium borohydride is added thereto at room temperature over 1 hour. After the addition, the mixture is stirred for one hour at room temperature, followed by concentrating the solution. Water is added to the residue and an isolated oily product is extracted with ethyl acetate. The organic solvent layer is washed with water, and dried. The solvent is distilled away. The residue is re-dissolved in dry ethyl acetate, and dry hydrogen chloride gas is bubbled thereinto to convert the compound in the solution to hydrochloride. Crystals are collected by filtration, and dried to obtain 3.4 g of crude hydrochloride. Recrystallization of this product from ethanol yields 2.91 g of 1-[2-hydroxy-2-(3,4-dibenzyloxyphenyl)-1-ethyl]-4-(2-keto-1-benzimidazolinyl)-piperidine hydrochloride.

m.p.: 138°–140° C.

IR absorption spectrum: 1695 cm$^{-1}$.

Elemental analysis: Calcd. for $C_{34}H_{36}ClN_3O_4$: C=69.67; H=6.19; N=7.17. Found: C=69.77; H=6.23; N=7.26.

Example 10

1.8 g of 1-[2-oxo-2-(2-naphthyl)-1-ethyl]-4-(2-keto-1-benzimidazolinyl)-piperidine obtained in the same manner as in Example 3 is suspended in 40 ml of methanol. 0.57 g of sodium borohydride is added by portions thereto at room temperature. After the addition, the mixture is stirred for 1.5 hours at room temperature and 50 ml of water is added to the reaction solution. Precipitates thus formed are collected by filtration and dried. Recrystallization from ethanol yields 1.63 g of 1-[2-hydroxy-2-(2-naphthyl)-1-ethyl]-4-(2-keto-1-benzimidazolinyl)-piperidine.

Example 11

1.47 g of 1-[2-oxo-2-(3,4-methylenedioxyphenyl)-1-ethyl]-4-(2-ethoxy-1-benzimidazolinyl)-piperidine obtained in the same manner as in Example 5 is suspended in 20 ml of methanol and cooled to 0°–5° C. 320 mg of sodium borohydride is added thereto over 30 minutes. After the addition, the mixture is stirred for 2 hours at 0°–5° C., and then methanol is distilled away under reduced pressure. Water and ethyl acetate are added to the residue, and the organic solvent layer is recovered. The organic solvent layer is washed with water, dried, and concentrated. Recrystallization of the residual crystals from ethanol yields 1.1 g of 1-[2-hydroxy-2-(3,4-methylenedioxyphenyl)-1-ethyl]-4-(2-ethoxy-1-benzimidazolinyl)-piperidine.

Example 12

A solution comprising 7.3 g of 1-[2-(3,4-methylenedioxyphenyl)-1-ethyl]-3-ethoxycarbonyl-4-piperidone, 2.5 g of o-phenylenediamine and 40 ml of xylene is heated to 130° C., and the water formed is removed using a Deen-Stark device. After 4 hours, heating and stirring are discontinued, and xylene is distilled away. 50 ml of ether is added to the residue. The mixture is stirred to form crystals. The crystals are collected by filtration and dried to obtain 1.5 g of crude crystals. Recrystallization thereof from ethanol yields 1.0 g of 1-[2-(3,4-methylenedioxyphenyl)-1-ethyl]-4-(2-keto-1-benzimidazolinyl)-1,2,5,6-tetrahydropyridine.

1-[2-(3,4-methylenedioxyphenyl)-1-ethyl]-3-ethoxycarbonyl-4-piperidone used as a starting material is obtained as follows.

A mixture of 16.5 g of 3,4-methylenedioxyphenylethylamine and 40.5 g of ethyl acrylate is refluxed for 24 hours over an oil bath. After cooling, the mixture is concentrated under reduced pressure to distill away excess ethyl acrylate. 16 g of N,N-bis (β-ethoxycarbonylethyl)-3,4-methylenedioxyphenylethylamine is obtained as the residue.

1.8 g of sodium hydride [50% (w/w) oil suspension] is suspended in 20 ml of dry xylene. To the suspension is gradually added dropwise a solution of 20 ml of xylene containing 13 g of the product obtained in the above-described reaction. The reaction is carried out at a temperature of 40°-50° C. When the reaction is almost completed, the reaction mixture is heated to 120° C. to complete the reaction. After cooling, water is added thereto and an organic solvent layer is recovered. After drying, the solvent is distilled away to obtain 7.3 g of a crude product as an oily material. The product is dissolved in ethyl acetate, and an equimolar amount of dry HCl gas is introduced thereinto to convert the product to hydrochloride. Recrystallization of the hydrochloride from ethanol yields 14 g of 1-[2-(3,4-methylenedioxyphenyl)-1-ethyl]-3-ethoxycarbonyl-4-piperidone hydrochloride.

m.p.: 176–186° C.

IR absorption specturm: 1670, 1630 cm$^{-1}$.

Elemental analysis: Calcd. for $C_{17}H_{22}ClNO$: C=57.39; H=6.23; N=3.94. Found: C=57.48; H=6.35; N=3.89.

Example 13

A mixture comprising 1.0 g of 1-[2-(3,4-methylenedioxyphenyl)-1-ethyl]-4-(2-keto-1-benzimidazolinyl)-1,2,5,6-tetrahydropyridine obtained in the same manner as in Example 12, 0.17 g of acetic acid, 100 ml of methanol, and 0.2 g of palladium carbon is poured to an autoclave and shaked at 45° C. under a hydrogen pressure of 10-5 atmospheric pressure. After 48 hours, shaking is discontinued, and the catalyst is removed by filtration. The mother liquor is concentrated, and the residue is dissolved in water. The pH of the solution is adjusted to 10.7 with 1 N caustic soda. Crystals thus formed are collected by filtration, washed with water, and then dried. The crude crystals are converted to hydrochloride in methanol to obtain 1.0 g of the crude hydrochloride. Recrystallization thereof from methanol yields 0.9 g of 1-[2-(3,4-methylenedioxyphenyl)-1-ethyl]-4-(2-keto-1-benzimidazolinyl)-piperidine hydrochloride.

Example 14

1.69 g of 1-[2-hydroxy-2-(3,4-dimethoxyphenyl)-1-ethyl]-4-(2-keto-1-benzimidazolinyl)-piperidine obtained in the same manner as in Example 8 is dissolved in trifluoroacetic acid. 1.5 g of triethylsilyl hydride is added to the solution, and vigorously stirred for 24 hours. Then, trifluoroacetic acid and triethylsilyl hydride are distilled away under reduced pressure. The residue is dissolved in 10 ml of ethyl acetate, and conc. sulfuric acid is added thereto until no additional white precipitates are formed by the addition. The precipitates formed are collected by filtration, dried, and dissolved in 10 ml of water. Then, the pH of the solution is adjusted to 10.5 with 2 N sodium hydroxide solution, and the mixture is extracted with chloroform. The extract chloroform layer is washed with water, and dried. The chloroform is distilled away to obtain 1.31 g of a crude product. Recrystallization of the product from ethyl acetate yields 0.9 g of 1-[2-(3,4-dimethoxyphenyl)-1-ethyl]-4-(2-keto-1-benzimidazolinyl)-piperidine.

Example 15

1 g of 1-[2-(3,4-methylenedioxyphenyl)-1-ethyl]-4-(2-keto-1-benzimidazolinyl)-piperidine hydrochloride obtained in the same manner as in Example 13 is suspended in 10 ml of chloroform. 25 g of boron tribromide is added thereto at room temperature, and the mixture is stirred for 3 days at room temperature. The reaction solution is then subjected to filtration, and the precipitate thus obtained is well washed with chloroform, and put in ice-water. After well stirring, the precipitate is collected by filtration. After washing with water and with ethanol, the crystals are dried to obtain 0.8 g of crude crystals. Recrystallization thereof from ethanol yields 0.69 g of 1-[2-(3,4-dihydroxyphenyl)-1-ethyl]-4-(2-keto-1-benzimidazolinyl)-piperidine hydrobromide.

Example 16

2.53 g of 1-(3,4-dimethoxyphenyl)-2-bromopropanone is added to a solution prepared by dissolving 2 g of 4-(2-keto-1-benzimidazolinyl)-piperidine and 0.95 g of triethylamine in 20 ml of chloroform. The resulting solution is refluxed for 5 hours over an oil bath. The same post-treatment as in Example 1 is conducted to obtain 3.02 g of a crude product. Recrystallization thereof from ethanol yields 2.7 g of 1-[3-oxo-3-(3,4-dimethoxyphenyl)-2-propyl]-4-(2-keto-1-benzimidazolinyl)-piperidine.

Example 17

4.2 g of 4-(2-keto-1-benzimidazolinyl)-piperidine, 2 g of triethylamine, 50 ml of chloroform, and 5.0 g of 1-(3,4-methylenedioxyphenyl)-2-bromopropanone are subjected to reaction under the same conditions as in Example 16 to obtain 7.0 g of a crude product. Recrystallization thereof from methanol yields 5.7 g of 1-[3-oxo-3-(3,4-methylenedioxyphenyl)-2-propyl]-4-(2-keto-1-benzimidazolinyl)-piperidine.

Example 18

1.4 g of 1-[3-oxo-(3,4-methylenedioxyphenyl)-2-propyl]-4-(2-keto-1-benzimidazolinyl)-piperidine obtained in the same manner as in Example 17 is suspended in 10 ml of methanol, and a solution prepared by introducing 0.13 g of dry hydrogen chloride gas into 3 ml of methanol is added thereto. After stirring the solution for 5 minutes at room temperature, the solvent is distilled away under reduced pressure. 10 ml of ether is added to the residue. The mixture is stirred and filtered to obtain 1.32 g of 1-[3-oxo-3-(3,4-methylenedioxyphenyl)-2-propyl]-4-(2-keto-1-benzimidazolinyl)-piperidine hydrochloride as powder. The powder is suspended in 10 ml of dry benzene, and 3.5 g of boron tribromide is added thereto. After stirring at room temperature for 24 hours, the mixture is subjected to filtration. Crystals thus obtained are put in water, well stirred, and filtered. The resultant crystals are dried to obtain 0.9 g of a crude product. Recrystallization thereof from water yields 0.7 g of 1-[3-oxo-3-(3,4-dihydroxyphenyl)-2-propyl]-4-(2-keto-1-benzimidazolinyl)-piperidine hydrobromide. When the product is subjected to silica gel chromatography using a mixture of n-butanol/acetic acid/water (4/1/1) as a developer, the product provides single spot at $R_f = 0.66$.

Example 19

2.5 g of 1-[3-oxo-3-(3,4-methylenedioxyphenyl)-2-propyl]-4-(2-keto-1-benzimidazolinyl)-piperidine obtained in the same manner as in Example 17 is suspended in 50 ml of methanol. 0.72 g of sodium borohydride is added thereto at room temperature over 30 minutes. After the addition, the mixture is heated to 40° C. After two hours, 100 ml of water is added to the reaction solution and the mixture is filtered. The residue is washed successively with water and methanol, and dried to obtain 2.0 g of crude crystals. Recrystallization of the crystals from methanol yields 1.6 g of 1-[3-hydroxy-3-(3,4-methylenedioxyphenyl)-2-propyl]-4-(2-keto-1-benzimidazolinyl)-piperidine.

Example 20

To 130 ml of a methanol solution containing 1.75 g of 1-[3-hydroxy-3-(3,4-dibenzyloxyphenyl)-2-propyl]-4-(2-keto-1-benzimidazolinyl)-piperidine is added 1 ml of a methanol solution containing 120 mg of hydrogen chloride, and, 0.2 g of palladium carbon is added thereto. The mixture is vigorously shaken in a hydrogen stream at room temperature. After stirring overnight, the catalyst is removed by filtration and the mother liquor is concentrated under reduced pressure. The resultant oily material is crystallized by adding a small amount of n-butanol. The crystals are collected by filtration, and dried to obtain 1.06 g of the crude crystals. Recrystallization thereof from n-butanol yields 0.8 g of 1-[3-hydroxy-3-(3,4-dihydroxyphenyl)-2-propyl]-4-(2-keto-1-benzimidazolinyl)-piperidine hydrochloride having m.p. 187°–189° C.

1-[3-hydroxy-3-(3,4-dibenzyloxyphenyl)-2-propyl]-4-(2-keto-1-benzimidazolinyl)-piperidine used as a starting material is prepared as follows.

1.52 g of 4-(2-keto-1-benzimidazolinyl)-piperidine, 0.8 g of triethylamine, 30 ml of chloroform, and 3.0 g of 1-(3,4-dibenzyloxyphenyl)-2-bromopropanone are subjected to reaction under the same conditions as in Example 16. 3.5 g of a crude product is recrystallized from either to obtain 3.4 g of 1-[3-oxo-3-(3,4-dibenzyloxyphenyl)-2-propyl]-4-(2-keto-1-benzimidazolinyl)-piperidine.

m.p.: 87°–90° C.

IR absorption spectrum: 1700–1680 cm$^{-1}$.

Elemental analysis: Calcd. for $C_{35}H_{35}N_3O_4 \cdot 0.5H_2O$: C=73.66; H=6.36; N=7.36. Found: C=73.92; H=6.18; N=7.35.

3.5 g of 1-[3-oxo-3-(3,4-dibenzyloxyphenyl)-2-propyl]-4-(2-keto-1-benzimidazolinyl)-piperidine obtained in the same manner as described above is suspended in a mixture solvent comprising 20 ml of methanol and 30 ml of ethanol, and reacted with 1.0 g of sodium borohydride in the same manner as in Example 19 to obtain 2.5 g of crude crystals. Recrystallization thereof from ethanol yields 2.0 g of 1-[3-hydroxy-3-(3,4-dibenzyloxyphenyl)-2-propyl]-4-(2-keto-1-benzimidazolinyl)-piperidine.

m.p.: 146°–148.5° C.

IR absorption spectrum: 1700 cm$^{-1}$

Elemental analysis: Calcd. for $C_{35}H_{37}N_3O_4$: C=74.57; H=6.62; N=7.46. Found: C=74.47; H=6.54; N=7.29.

Example 21

0.7 g of 1-[3-oxo-3-(3-benzyloxyphenyl)-2-propyl]-4-(2-keto-1-benzimidazolinyl)-piperidine is dissolved in 50 ml of methanol, and 1 ml of methanol solution containing 0.1 g of hydrogen chloride is added thereto. Further, 0.2 g of palladium-carbon is added to the solution, and the mixture is shaked in an autoclave at room temperature with a hydrogen pressure of 10 atmospheric pressures to reduce the compound. After 24 hours, the reaction solution is subjected to filtration, and the mother liquor is concentrated under reduced pressure. Ethyl acetate is added to the residue, and filtered. The mixture is dried to obtain 0.55 g of 1-[3-hydroxy-(3-hydroxyphenyl)-2-propyl]-4-(2-keto-1-benzimidazolinyl)piperidine hydrochloride as powder.

1-[3-oxo-3-(3-benzyloxyphenyl)-2-propyl]-4-(2-keto-1-benzimidazolinyl)-piperidine used as a starting material is prepared as follows.

2.2 g of 1-(3-benzyloxyphenyl)-2-bromopropanone is added to a solution prepared by dissolving 1.5 g of 4-(2-keto-1-benzimidazolinyl)-piperidine and 0.2 g of triethylamine in 6 ml of chloroform. The solution is refluxed for 5 hours over an oil bath. The same post-treatment as in Example 1 is conducted to obtain 2.3 g of a crude product. Recrystallization of the product from ethyl acetate yields 2.0 g of 1-[3-oxo-3-(3-benzyloxyphenyl)-2-propyl]-4-(2-keto-1-benzimidazolinyl)-piperidine.

m.p: 138°–140° C.

IR absorption spectrum: 1705, 1695 cm$^{-1}$

Elemental analysis: Calcd. for $C_{28}H_{29}N_3O_3$: C=73.82; H=6.42; N=9.23. Found: C=73.80; H=6.41; N=9.13.

Example 22

1.4 g of 1-[3-oxo-3-(3,4-dimethoxyphenyl)-2-propyl]-4-(2-keto-1-benzimidazolinyl)-piperidine obtained in the same manner as in Example 16 is suspended in 50 ml of methanol, and reacted with 230 mg of sodium borohydride in the same manner as in Example 19 to obtain 1.3 g of crude crystals. Recrystallization thereof from methanol yields 1.2 g of 1-[3-hydroxy-3-(3,4-dimethoxyphenyl)-2-propyl]-4-(2-keto-1-benzimidazolinyl)-piperidine.

Example 23

1 g of 1-[2-hydroxy-2-(3,4-methylenedioxyphenyl)-1-ethyl]-4-(2-keto-1-benzimidazolinyl)-piperidine obtained in the same manner as in Example 7 is dissolved in 7 ml of dimethylformamide, and 270 mg of acetic anhydride is added thereto at 0° C. After the addition, the mixture is stirred overnight at room temperature and dimethylformamide is distilled away under reduced pressure. The residue is dissolved in 20 ml of chloroform. 1 ml of triethylamine is added to the solution, and stirred. Then, water is added thereto and well shaked.

The chloroform layer is recovered, washed several times with 10 ml of water, and dried. Chloroform is distilled away to obtain 1.0 g of a crude product. The product is subjected to silica gel chromatography using chloroform as a developer to obtain 0.8 g of 1-[2-acetoxy-2-(3,4-methylenedioxyphenyl)-1-ethyl]-4-(2-keto-1-benzimidazolinyl)piperidine as an oily material.

Example 24

To a solution comprising 2.3 g of 4-(2-keto-1-benzimidazolinyl)-piperidine, 1.1 g of triethylamine, and 20 ml of chloroform is added 2.2 g of phenacyl bromide, and the reaction is carried out under the same conditions as in Example 1. The same post-treatment as in Example 1 is conducted to obtain 3.2 g of a crude product. Recrystallization of the product from a mixture solution of ethanol and ethyl acetate (2:3 by volume) yields 2.92 g of 1-[2-oxo-2-phenyl-1-ethyl]-4-(2-keto-1-benzimidazolinyl)-piperidine.

Example 25

1.91 g of the product obtained in Example 24 is dissolved in 30 ml of methanol, and reacted with 1.1 g of sodium borohydride under the same conditions as in Example 7 to obtain 1.62 g of a crude product. Recrystallization of the product from ethanol yields 1.3 g of 1-[2-hydroxy-2-phenyl-1-ethyl]-4-(2-keto-1-benzimidazolinyl)-piperidine.

Example 26

A solution comprising 1.1 g of 4-(3-ethyl-1-benzimidazolinyl)-piperidine hydrochloride, 0.8 g of triethylamine, 960 mg of 3,4-methylenedioxy-α-bromoacetophenone, and 20 ml of dichloromethane is subjected to reaction under the same conditions as in Example 5. The mixture is subjected to the same post-treatment as in Example 1 to obtain 1.45 g of crude crystals. Recrystallizaion thereof from ethanol yields 1.2 g of 1-[2-oxo-2-(3,4-methylenedioxyphenyl)- 1-ethyl]-4-(3-ethyl-2-keto-1-benzimidazolinyl)-piperdine.

Example 27

1.25 g of the product obtained in Example 26 is dissolved in 50 ml of methanol. 300 mg of sodium borohydride is added thereto over 30 minutes at room temperature, and the mixture is stirred for one hour at the same temperature. Then, the same post-treatment as in Example 11 is conducted to obtain a crude product. Recrystallization thereof from ethanol yields 0.9 g of 1-[2-hydroxy-2-(3,4-methylenedioxyphenyl)-1-ethyl]-4-(3-ethyl-2-keto-1-benzimidazolinyl)-piperidine.

Example 28

To a solution comprising 15 g of 4-(2-keto-1-benzimidazolinyl)-piperidine, 7 g of triethylamine and 100 ml of chloroform is added 20 g of 3,4,5-trimethoxy-α-bromoacetophenone. The similar procedures as in Example 1 are repeated to obtain 13.4 g of crude crystals. Recrystallization of the crystals from ethyl acetate yields 9.2 g of 1-[2-oxo-2-(3,4,5-trimethoxyphenyl)-1-ethyl]-4-(2-keto-1-benzimidazolinyl)-piperidine.

Example 29

6.0 g of crude crystals of 1-[2-oxo-2-(3,4,5-trimethoxyphenyl)-1-ethyl]-4-(2-keto-1-benzimidazolinyl)-piperidine obtained in the same manner as in Example 28 is dissolved in 150 ml of methanol. 850 mg of sodium borohydride is added thereto at room temperature over one hour. After the addition, the mixture is stirred at room temperature for one hour and is concentrated. Water is added to the residue and the resultant oily material is extracted with ethyl acetate. The organic solvent layer is washed with water and then dried. The solvent is distilled away to obtain 5.2 g of crude crystals. Recrystallization of the crystals from ethanol yields 4.8 g of 1-[2-hydroxy-(3,4,5-trimethoxyphenyl)-1-ethyl]-4-(2-keto-1-benzimidazolinyl)-piperidine.

Example 30

To a solution comprising 4.34 g of 4-(2-keto-1-benzimidazolinyl)-piperidine, 2.1 g of triethylamine and 50 ml of chloroform is added 6.06 g of 1-(3,4,5-trimethoxyphenyl)-2-bromopropanone. The solution is refluxed for 8 hours over oil bath. The same post-treatment as in Example 1 is conducted to obtain 7.6 g of crude crystals. Recrystallization of the crystals from ethanol yields 6.1 g of 1-[-3-oxo(3,4,5-trimethoxyphenyl)-2-propyl]-4-(2-keto-1-benzimidazolinyl)-piperidine.

Example 31

3.9 g of 1-[3-oxo-3-(3,4,5-trimethoxyphenyl)-2-propyl]-4-(2-keto-1-benzimidazolinyl)-piperidine obtained in the same manner as in Example 30, is suspended in 70 ml of methanol. 400 mg of sodium borohydride is added thereto and the reaction is carried out as in the same manner as in Example 19 to obtain 3.8 g of crude crystals. Recrystallization of the crystals from ethanol yields 2.83 g of 1-[3-hydroxy-3-(3,4,5-trimethoxyphenyl)-2-propyl]-4-(2-keto-1-benzimidazolinyl)-piperidine.

Example 32

To a solution of 2.0 g of 1-[3-hydroxy-3-(3,4-dimethoxyphenyl)-2-propyl]-4-(2-keto-1-benzimidazolinyl)-piperidine and 1.2 g of 4-dimethylaminopyridine in 10 ml of dimethylformamide is added 1.02 g of anhydrous acetic acid and the mixture is stirred at room temperature for 12 hours. Dimethylformamide is distilled away under reduced pressure. The resulting residue is dissolved in 20 ml of ethyl acetate. To the solution is added 1.1 g of triethylamine. The mixture is washed five times with 20 ml of water and dried. The solvent is distilled away to obtain crude crystals. Recrystallization of the crystals from ethyl acetate yields 1.65 g of 1-[3-acetoxy-3-(3,4-dimethoxyphenyl)-2-propyl]-4-(3-acetyl-2-keto-1-benzimidazolinyl)-piperidine.

Example 33

A solution of 2.0 g of 1-[3-hydroxy-3-(3,4-dimethoxyphenyl)-2-propyl]-4-(2-keto-1-benzimidazolinyl)-piperidine and 0.6 g of 4-dimethylaminopyridine in 10 ml of dimethylformamide is stirred at room temperature for 12 hours. Dimethylformamide is distilled away under reduced pressure to obtain a residue. The residue is dissolved in 20 ml of ethyl acetate. To the solution is added 0.6 g of triethylamine. The mixture is washed five times with 20 ml of water and dried. Recrystallization of the crystals from a mixture of dioxane and ether (1:1) yields 1.21 g of 1-[3-hydroxy-3-(3,4-dimethoxyphenyl)-2-propyl]-4-(3-acetyl-2-keto-1-benzimidazolinyl)-piperidine.

Example 34

In this Example, 0.7 g of 1-[3-acetoxy-3-(3,4-dimethoxyphenyl)-2-propyl]-4-(3-acetyl-2-keto-1-benzimidazolinyl)-piperidine is dissolved in a mixture of 2 ml of chloroform and 1 ml of methanol. To the solution is added 0.7 g of magnesium perchlorate and the mixture is stirred at room temperature for 2 minutes. Water is added to the reaction solution and the mixture is stirred. The chloroform layer is recovered and washed 2 times with water. The washed solution is dried and chloroform is distilled away. The resulting residue is recrystallized from dioxane to obtain 550 mg of 1-[3-acetoxy-3-(3,4-dimethoxyphenyl)-2-propyl]-4-(2-keto-1-benzimidazolinyl)-piperidine.

Example 35

To a solution of 1.43 g of the hydrochloride of 4-(2-keto-3-ethoxycarbonyl-1-benzimidazolinyl)-piperidine and 890 mg of triethylamine in 10 ml of chloroform is added 1.14 g of 3,4-dimethoxy-α-bromoacetophenone and the mixture is stirred at room temperature for 5 hours. The mixture is concentrated. To the residue are added water and ethyl acetate. The mixture is shaked and subjected to separation. The organic solvent layer is washed and dried. The solvent is distilled away under reduced pressure to obtain an oily residue. The residue is dissolved in 5 ml of acetone and 520 mg of succinic acid is added. The mixture is stirred. Resulting crystals are recovered by filtration and dried. Recrystallization of the crystals from dioxane yields 1.35 g of the succinate of 1-[2-oxo-2-(3,4-dimethoxyphenyl)-1-ethyl]-4-(2-keto-3-ethoxy-carbonyl-1-benzimidazolinyl)piperidine.

The hydrochloride of 4-(2-keto-3-ethoxycarbonyl-1-benzimidazolinyl)-piperidine used as the starting compound is prepared as follows.

A suspension of 165 mg of sodium hydride in 10 ml of tetrahydrofuran is cooled at 0° C. To the suspension is added dropwise a solution of 2.2 g of 1-t-butyloxycarbonyl-4-(2-keto-1-benzimidazolinyl)-piperidine in 18 ml of tetrahydrofuran over 30 minutes in a stream of nitrogen. The mixture is stirred at room temperature for 2 hours and 760 mg of ethoxycarbonylchloride is added. The mixture is stirred at room temperature for one hour and 300 mg of ethoxycarbonylchloride is added. The mixture is stirred for 12 hours. The reaction solution is put into ice and the resulting oily product is extracted with ethyl acetate. The extract is washed and dried. Ethyl acetate is distilled away and the resulting residue is recrystallized from n-hexane to obtain 2.4 g of 1-t-butyloxycarbonyl-4-(2-keto-3-ethoxycarbonyl-1-benzimidazolinyl)-piperidine.

m.p. : 89°–91° C.

IR absorption spectrum: 1750, 1710 cm$^{-1}$.

Elemental analysis: Calcd. for $C_{20}H_{17}N_3O_5$: C=61.88, H=6.99, N=10.79. Found: C=61.68, H=7.07, N=10.73.

3.2 g of 1-t-butyloxycarbonyl-4-(2-keto-3-ethoxycarbonyl-1-benzimidazolinyl)-piperidine is dissolved in 26 ml of ethyl acetate. The solution is cooled at 0° C. To the solution is added dropwide 17.8 ml of 5.7 N hydrochloric acid in ethyl acetate. The mixture is stirred at 0° C. for 15 hours and the resulting crystals are recovered by filtration. The crystals are dried to obtain 2.7 g of the hydrochloride of 4-(2-keto-3-ethoxycarbonyl-1-benzimidazolinyl)-piperidine.

m.p.: 184°–185° C.

IR absorption spectrum: 1790, 1745, 1730, 1695, 1682 cm$^{-1}$.

Elemental analysis: Calcd. for $C_{15}H_{19}N_3O_3 \cdot HCL$: C=55.30; H=6.19; N=12.90. Found: C=55.04; H=6.38; N=12.87.

Example 36

| (Example of preparing 10,000 5 mg-tablets) | |
|---|---|
| Compound 7 | 50 g |
| Magnesium stearate | 4 g |
| Crystalline cellulose | 746 g |

The above-described ingredients are mixed for 5 minutes by means of a mixer. The resulting mixed powder is made into 10,000 tablets of 6.0 mm in diameter, 2.5 mm in thickness, and 80 mg in weight using a tablet-making machine (Model HU-37; made by Kikusui Seisakusho) equipped with a pestle having a plane surface and round corners.

Example 37

| Compound 9 | 55 g |
|---|---|
| Magnesium stearate | 4 g |
| Crystalline cellulose | 741 g |

The above-described ingredients are processed in the same manner as in Example 36 to obtain tablets.

Example 38

| Compound 20 | 56 g |
|---|---|
| Magnesium stearate | 4 g |
| Crystalline cellulose | 740 g |

The above-described ingredients are processed in the same manner as in Example 36 to obtain tablets.

Example 39

| (Example of preparing a powder) | |
|---|---|
| Compound 21 | 110 g |
| Lactose | 890 g |

The above-described ingredients are mixed for 10 minutes using a mixer to obtain a uniform mixture (powder).

Example 40

| Compound 1 | 109 g |
|---|---|
| Lactose | 891 g |

The above-described ingredients are mixed for 10 minutes using a mixer to obtain a uniform mixture (powder).

We claim:

1. A compound represented by the formula:

$$Ar-Q-\underset{R}{CH}-N\bigcirc-Z$$

wherein Ar represents a naphthyl, phenyl or substituted phenyl group having 1 to 5 substituents wherein the substituent is a straight or branched-chain alkoxy group having 1 to 6 carbon atoms, a hydroxy group, a benzyloxy group or an alkylenedioxy group having 1 to 3 carbon atoms; Q represents

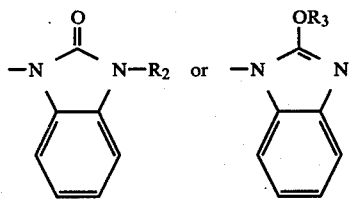

wherein $R_1$ represents a hydrogen atom, an alkyl group having 1 to 5 carbon atoms or an alkanoyl group having 2 to 6 carbon atoms; R represents a hydrogen atom or an alkyl group having 1 to 5 carbon atoms; and Z represents

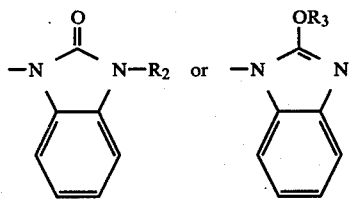

wherein $R_2$ is a hydrogen atom, an alkyl group having 1 to 5 carbon atoms, an alkanoyl group having 2 to 6 carbon atoms or an alkoxycarbonyl group having 2 to 6 carbon atoms and $R_3$ is an alkyl group having 1 to 5 carbon atoms; or a pharmaceutically acceptable acid addition salt thereof.

2. The compound according to claim 1, wherein said acid addition salt is selected from the group consisting of hydrochloride, hydrobromide, hydroiodide, sulfate, phosphate, acetate, benzoate, maleate, fumarate, succinate, tartrate, citrate, oxalate, glyoxylate, aspartate and methanesulfonate.

3. The compound according to claim 1, wherein Ar is a substituted phenyl group and said substituent is a hydroxy, alkoxy or alkylenedioxy group.

4. The compound according to claim 1, wherein Ar is a substituted phenyl group and said substituted phenyl group has 1–5 substituents on the phenyl ring.

5. The compound according to claim 1, wherein Ar is 3,4-dihydroxyphenyl, 3-hydroxyphenyl, 3,4-dimethoxyphenyl, 3,4-methylenedioxyphenyl, 3,4,5-trimethoxyphenyl, 3,4-dibenzyloxyphenyl, 3-benzyloxyphenyl, phenyl, or 2-naphthyl.

6. The compound according to claim 1 wherein Q is

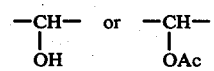

7. The compound according to claim 1, wherein Z is

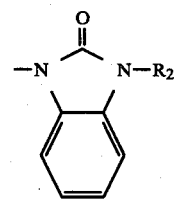

and $R_2$ is a hydrogen atom or an ethyl, acetyl or ethyloxycarbonyl group.

8. The compound according to claim 1, wherein Z is

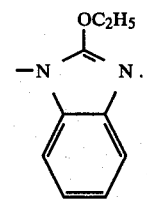

9. A compound which is 1-[2-(3,4-dihydroxyphenyl)-2-hydroxy]ethyl-4-(2-oxobenzimidazolin-1-yl)piperidine.

10. A compound represented by the formula

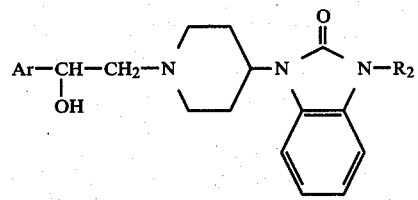

wherein Ar represents a 3-hydroxy-substituted phenyl group or a 3,4-dihydroxy-substituted phenyl group and $R_2$ represents hydrogen or an alkyl group having 1 to 5 carbon atoms; or a pharmaceutically acceptable acid addition salt thereof.

11. A hypotensive composition which comprises an effective hypotensive amount of the compound defined in claim 1 and a pharmaceutically acceptable carrier.

12. The composition according to claim 11, wherein said composition is in a form for oral administration.

13. The composition according to claim 11, wherein said composition is in a form of suspension, syrup, powder, pill, capsule or tablet.

* * * * *

UNITED STATES PATENT AND TRADEMARK OFFICE
CERTIFICATE OF CORRECTION

PATENT NO. : 4,446,141
DATED      : May 1, 1984
INVENTOR(S) : NOBUHIRO NAKAMIZO, et al.

It is certified that error appears in the above-identified patent and that said Letters Patent is hereby corrected as shown below:

Column 4, lines 60-67, change the formula to read as follows:

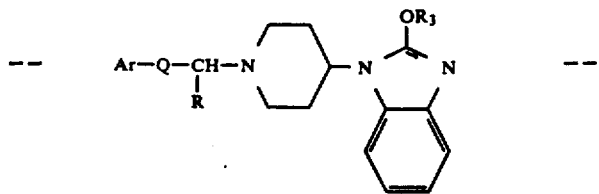

Column 12, line 31, the values listed under:
    "Dose (mg/kg)
    0.1  0.5  1.0  10  50" should read:
    --  --  -17  --  -- 40  --

Column 13, line 53, change "reductions" to --reactions--
Column 27, line 59, change "either" to --ether--

Signed and Sealed this

Sixteenth Day of October 1984

[SEAL]

Attest:

GERALD J. MOSSINGHOFF

Attesting Officer    Commissioner of Patents and Trademarks